(12) United States Patent
Kanias et al.

(10) Patent No.: US 8,198,085 B2
(45) Date of Patent: *Jun. 12, 2012

(54) SOMATIC CELLS FOR USE IN CELL THERAPY

(75) Inventors: Tamir Kanias, Givat Shmuel (IL); Yehudit Natan, Holon (IL)

(73) Assignee: Core Dynamics Limited, Hamilton HM EX (BM)

( * ) Notice: Subject to any disclaimer, the term of this patent is extended or adjusted under 35 U.S.C. 154(b) by 625 days.

This patent is subject to a terminal disclaimer.

(21) Appl. No.: 11/989,929

(22) PCT Filed: Aug. 3, 2006

(86) PCT No.: PCT/IL2006/000902
§ 371 (c)(1),
(2), (4) Date: Apr. 16, 2008

(87) PCT Pub. No.: WO2007/015252
PCT Pub. Date: Feb. 8, 2007

(65) Prior Publication Data
US 2010/0105133 A1    Apr. 29, 2010

Related U.S. Application Data

(60) Provisional application No. 60/704,917, filed on Aug. 3, 2005.

(51) Int. Cl.
*C12N 5/00* (2006.01)
*C12N 5/02* (2006.01)
*C12N 5/07* (2010.01)
*C12N 5/10* (2006.01)

(52) U.S. Cl. ......... 435/374; 435/366; 435/354; 435/363

(58) Field of Classification Search .................. None
See application file for complete search history.

(56) References Cited

U.S. PATENT DOCUMENTS

| | | |
|---|---|---|
| 3,074,247 A | 1/1963 | Polk |
| 3,347,745 A | 10/1967 | Rinfret et al. |
| 4,018,911 A | 4/1977 | Lionetti et al. |
| 4,117,881 A | 10/1978 | Williams et al. |
| 4,480,682 A | 11/1984 | Kaneta et al. |
| 4,620,908 A | 11/1986 | Van Duzer |
| 4,857,319 A | 8/1989 | Crowe et al. |
| 4,874,690 A | 10/1989 | Goodrich, Jr. et al. |
| 5,059,518 A | 10/1991 | Kortright et al. |
| 5,071,598 A | 12/1991 | Baldeschwieler et al. |
| 5,131,850 A | 7/1992 | Brockbank |
| 5,364,756 A | 11/1994 | Livesey et al. |
| 5,418,130 A | 5/1995 | Platz et al. |
| 5,587,490 A | 12/1996 | Goodrich, Jr. et al. |
| 5,629,145 A | 5/1997 | Meryman |
| 5,709,992 A | 1/1998 | Rubinstein |
| 5,827,741 A | 10/1998 | Beattie et al. |
| 5,843,780 A | 12/1998 | Thomson |
| 5,863,715 A | 1/1999 | Rajotte et al. |
| 5,869,092 A | 2/1999 | Hays et al. |
| 5,873,254 A | 2/1999 | Arav |
| 5,897,987 A | 4/1999 | Oliver et al. |
| 5,955,257 A | 9/1999 | Burger et al. |
| 6,007,978 A | 12/1999 | Goodrich, Jr. et al. |
| 6,073,540 A | 6/2000 | Garrett |
| 6,146,890 A | 11/2000 | Danon |
| 6,319,914 B1 | 11/2001 | Simpkins et al. |
| 6,337,205 B1 | 1/2002 | Wisniewski |
| 6,453,683 B1 | 9/2002 | Wisniewski et al. |
| 6,482,585 B2 | 11/2002 | Dottori |
| 6,488,033 B1 | 12/2002 | Cerundolo |
| 6,723,497 B2 | 4/2004 | Wolkers et al. |
| 6,740,484 B1 | 5/2004 | Khirabadi et al. |
| 6,887,704 B2 | 5/2005 | Peled et al. |
| 2002/0119946 A1 | 8/2002 | Gen |
| 2002/0177116 A1 | 11/2002 | Wiggins et al. |
| 2003/0059338 A1 | 3/2003 | Mann et al. |
| 2003/0068416 A1 | 4/2003 | Burgess et al. |
| 2004/0006999 A1 | 1/2004 | Brown et al. |
| 2004/0067157 A1 | 4/2004 | MacPhee et al. |

(Continued)

FOREIGN PATENT DOCUMENTS

DE    100 56 181 C1    3/2002

(Continued)

OTHER PUBLICATIONS

Ahlenstiel, et al., "Bioflavonoids attenuate renal proximal tubular cell injury during cold preservation in Euro-Collins and University of Wisconsin solutions", Kidney International, vol. 63, pp. 554-563, (2003). XP-002337114.

Chen, et al., "Beneficial Effect of Intracellular Trehalose on the Membrane Integrity of Dried Mammalian Cells", Cryobiology, vol. 43, pp. 168-181, (2001).

Chow, et al., "Phase I Pharmacokinetic Study of Tea Polyphenols following Single-dose Administration of Epigallocatechin Gallate and Polyphenon E", Cancer Epidemiology, Biomarkers & Prevention, vol. 10, pp. 53-58, (2001).

Crowe, et al., "Stabilization of membranes in human platelets freeze-dried with trehalose", Chemistry and Physics of Lipids, vol. 122, pp. 41-52, (2003).

(Continued)

*Primary Examiner* — Doug Schultz
(74) *Attorney, Agent, or Firm* — Vorys, Sater, Seymour and Pease LLP; Susanne M. Hopkins; Ari G. Zytcer

(57) ABSTRACT

The present invention generally concerns cell therapy and products for use in such therapy. Particularly, the invention provides a preserved cell preparation essentially free of one or more members of a group of cryoprotecting agents consisting of polyalcohols, DMSO and cryoprotecting proteins, the preserved cell preparation comprising somatic cells and at least one polyphenol, wherein upon reconstitution of cells in the cell preparation, at least a portion of said stem cells are viable, said portion being sufficient for use of the cell preparation in stem cell therapy. The invention also provides cells reconstituted from preserved somatic cells, and the use of the reconstituted cells in cell therapy. A preferred cell preparation in accordance with the invention comprises stem cells, preferably human stem cells.

7 Claims, 6 Drawing Sheets

U.S. PATENT DOCUMENTS

| | | | |
|---|---|---|---|
| 2004/0129003 | A1 | 7/2004 | Voute et al. |
| 2004/0191754 | A1 | 9/2004 | Meir et al. |
| 2004/0197310 | A1 | 10/2004 | Sanberg et al. |
| 2005/0008623 | A1 | 1/2005 | Bechetoille et al. |
| 2005/0020524 | A1 | 1/2005 | Boyd |
| 2005/0042754 | A1 | 2/2005 | Miyazaki et al. |
| 2005/0059152 | A1 | 3/2005 | Tanavde et al. |
| 2005/0095228 | A1 | 5/2005 | Fraser et al. |
| 2005/0118712 | A1 | 6/2005 | Tsai et al. |
| 2005/0142118 | A1 | 6/2005 | Wernet |
| 2006/0035383 | A1 | 2/2006 | Ho et al. |
| 2006/0057555 | A1 | 3/2006 | Damari et al. |
| 2007/0077237 | A1 | 4/2007 | Damari et al. |
| 2007/0077535 | A1 | 4/2007 | Wichmann et al. |
| 2008/0120984 | A1 | 5/2008 | Shaham et al. |

FOREIGN PATENT DOCUMENTS

| | | | |
|---|---|---|---|
| EP | 0 664 080 A1 | | 7/1995 |
| EP | 0 668 013 A2 | | 8/1995 |
| EP | 1 057 405 A1 | | 12/2000 |
| EP | 1 131 998 A1 | | 9/2001 |
| EP | 1 471 140 A1 | | 10/2004 |
| EP | 1 535 514 A1 | | 6/2005 |
| EP | 1 627 565 A1 | | 2/2006 |
| GB | 1 279 356 | | 6/1972 |
| JP | 2000-189155 A | | 7/2000 |
| RU | 1806692 A1 | | 4/1993 |
| WO | 91/06213 A1 | | 5/1991 |
| WO | 91/16060 A1 | | 10/1991 |
| WO | 93/00806 A1 | | 1/1993 |
| WO | 97/35472 A1 | | 10/1997 |
| WO | 97/39104 A1 | | 10/1997 |
| WO | 98/10231 A1 | | 3/1998 |
| WO | 98/46072 A1 | | 10/1998 |
| WO | 99/60849 A1 | | 12/1999 |
| WO | 00/29551 A2 | | 5/2000 |
| WO | 01/23532 A1 | | 4/2001 |
| WO | 01/45503 A2 | | 6/2001 |
| WO | 01/50852 A2 | | 7/2001 |
| WO | 01/87062 A2 | | 11/2001 |
| WO | 02/01952 A1 | | 1/2002 |
| WO | 02/32225 A2 | | 4/2002 |
| WO | 02/076206 A2 | | 10/2002 |
| WO | 03/020874 A2 | | 3/2003 |
| WO | 03/056919 A2 | | 7/2003 |
| WO | 03/099040 A1 | | 12/2003 |
| WO | 2004/009138 A2 | | 1/2004 |
| WO | 2004/055456 A1 | | 7/2004 |
| WO | 2004/098285 A2 | | 11/2004 |
| WO | 2005/032251 A1 | | 4/2005 |
| WO | WO 2005/004398 | * | 5/2005 |
| WO | 2005/056755 A2 | | 6/2005 |
| WO | 2005/072523 A2 | | 8/2005 |
| WO | 2005/072790 A1 | | 8/2005 |
| WO | 2006/016372 A1 | | 2/2006 |
| WO | 2008/032314 A2 | | 3/2008 |

OTHER PUBLICATIONS

Csönge, et al., "Banking of osteochondral allografts, Part II. Preservation of Chondrocyte Viability During Long-Term Storage", Cell and Tissue Banking, vol. 3, pp. 161-168, (2002). XP-002313332.

De Korte, et al., "Quality Determinants of Erythrocyte Destined for Transfusion", Cellular and Molecular Biology, vol. 50, No. 2, pp. 187-195, (2004).

Fujiki, et al., "Mechanistic Findings of Green Tea as Cancer Preventive for Humans", P.S.E.B.M., vol. 220, pp. 225-228, (1999).

Galati, et al., "Prooxidant activity and cellular effects of the phenoxyl radicals of dietary flavonoids and other polyphenolics", Toxicology, vol. 177, pp. 91-104, (2002).

Gao, et al., "Development of a Directional Solidification Device for Cell Cryopreservation", Cell Preservation Technology, vol. 1, No. 4, pp. 231-238, (2003).

Goodrich, et al., "Preservation of metabolic activity in lyophilized human erythrocytes", Proc. Natl. Acad. Sci. USA, vol. 89, pp. 967-971, (1992).

Grinberg, et al., "Protective Effects of Tea Polyphenols against Oxidative Damage to Red Blood Cells", Biochemical Pharmacology, vol. 54, pp. 973-978, (1997).

Han, et al., "Protection of osteoblastic cells from freeze/thaw cycle-induced oxidative stress by green tea polyphenol", Biotechnology Letters, vol. 27, pp. 655-660, (2005).

Higgs, et al., "Cartilage Regeneration and Repair, Where Are We?" Proceedings of the International Cartilage Repair Society's Second Symposium, (1998).

Isbrucker, et al., "Safety studies on epigallocatechin gallate (EGCG) preparations. Part 3: Teratogenicity and reproductive toxicity studies in rats", Food Chemical Toxicology, vol. 44, pp. 651-661, (2006).

Jomha, et al., "Cryopreservation of intact human articular cartilage", Journal of Orthopaedic Research, vol. 20, pp. 1253-1255, (2002).

Kumazawa, et al., "Direct Evidence of Interaction of a Green Tea Polyphenol, Epigallocatechin Gallate, with Lipid Bilayers by Solid-state Nuclear Magnetic Resonance", Biosci. Biotechnol. Biochem., vol. 68, No. 8, pp. 1743-1747, (2004).

Kusakabe, et al., "Maintenance of genetic integrity in frozen and freeze-dried mouse spermatozoa", Proc Natl Acad Sci U S A, vol. 98, No. 24, pp. 13501-13506, (2001).

Kushibe, et al., "Tracheal Allotransplantation Maintaining Cartilage Viability with Long-Term Cryopreserved Allografts", Ann Thorac Surg, vol. 71, pp. 1666-1669, (2001).

Laprade, et al., "Refrigerated Osteoarticular Allografts to Treat Articular Cartilage Defects of the Femoral Condyles. A Prospective Outcomes Study", J Bone Joint Surg Am, vol. 91, pp. 805-811, (2009).

Lelkens, et al., "Stability after thawing of RBCs frozen with the high- and low-glycerol method", Transfusion, vol. 43, pp. 157-164, (2003).

López, et al., "Determination of Viability of Human Cartilage Allografts by a Rapid and Quantitative Method Not Requiring Cartilage Digestion", Cell Transplantation, vol. 17, pp. 859-864, (2008).

McGoveran, et al., "Long-Term Chondrocyte Viability in a Fresh Osteochondral Allograft", The Journal of Knee Surgery, vol. 15, No. 2, pp. 97-100, (2002).

Muldrew, et al., "Localization of Freezing Injury in Articular Cartilage", Cryobiology, vol. 31, pp. 31-38, (1994).

Muldrew, "Cryopreservation of Articular Cartilage", Abstracts, 33rd Annual Meeting of the Society for Cryobiology, pp. 616-617, No. 6, Indianapolis, Indiana, Aug. 21, 1996.

Muldrew, et al., "Cryobiology of Articular Cartilage: Ice Morphology and Recovery of Chondrocytes", Cryobiology, vol. 40, pp. 102-109, (2000).

Muldrew, et al., "Transplantation of Articular Cartilage Following a Step-Cooling Cryopreservation Protocol", Cryobiology, vol. 43, pp. 260-267, (2001.

Muldrew, et al., "Chondrocyte Sensitivity to Lethal Injury Correlates with Proximity to the Cartilage Surface", Abstracts, 32nd Annual Meeting of the Orthopaedic Research Society, pp. 589, No. 136, New Orleans, Louisiana, Feb. 1986.

Pegg, et al., "Fractures in Cryopreserved Elastic Arteries", Cryobiology, vol. 34, pp. 183-192, (1997).

Rzepakovsky, "The Effect of Long Term Storage at -80° C on the Cell Viabillity in Cartilage Tissue", Study Report, No. LAB-0161, 3 pages, (2005).

Rzepakovsky, "The Effect of Long Term Storage in Liquid Nitrogen on the Cell Viabillity in Cartilage Tissue", Study Report, No. LAB-0161, 3 pages, (2006).

Satpathy, et al., "Loading red blood cells with trehalose: a step towards biostabilization", Cryobiology, vol. 49, pp. 123-136, (2004).

Schachar, et al., "Transplantation of Cryopreserved Osteochondral Dowel Allografts for Repair of Focal Articular Defects in an Ovine Model", The Journal of Bone and Joint Surgery, Inc., vol. 17, pp. 909-920, (1999).

Dimethyl sulfoxide, SIGMA Product Information, 2 pages, Dec. 2003.

Suganuma, et al., "Green tea and cancer chemoprevention", Mutation Research, vol. 428, pp. 339-344, (1999).

Teng, et al., "Enhancing Osteochondral Allograft Viability", Clin Orthop Relat Res, vol. 466, pp. 1804-1809, (2008).

Towns, "Moisture content in proteins: its effects and measurement", Journal of Chromatography A, vol. 705, pp. 115-127, (1995).

Van Steensel, et al., "Optimization of cryopreservative procedures for human articular cartilage chondrocytes", Arch Orthop Trauma Surg, vol. 113, pp. 318-321, (1994).

Williams, et al., "Prolonged Storage Effects on the Articular Cartilage of Fresh Human Osteochondral Allografts", J Bone Joint Surg Am, vol. 85, pp. 2111-2120, (2003).

Williams, et al., "Analysis of Cartilage Tissue on a Cellular Level in Fresh Osteochondral Allograft Retrievals", Am J Sports Med, vol. 35, No. 12, pp. 2022-2032, (2007).

Williams, et al., "Controversies in Knee Surgery", Controversies in Orthopaedic Surgery, pp. 462-463, Oxford University Press, 2004.

XP-002337043: Derwent, "Preservation solution for cells and tissues contains polyphenol as effective component", 1 page, (2002).

XP-002337044: Derwent, "Composition for preservative of animal cell, organs such as skin, blood vessel, cornea, kidney, heart, liver, lungs, placenta or pancreas, contains preset amount of epigallocatechin gallate as active ingredient", 1 page, (2003).

Zoberi, et al., "Radiosensitizing and anti-proliferative effects of resveratrol in two human cervical tumor cell lines", Cancer Letters, vol. 175, pp. 165-173, (2002).

Ptak, et al., "Improving Delivery and Offspring Viability of in Vitro-Produced and Cloned Sheep Embryos", Biology of Reproduction, vol. 67, pp. 1719-1725, (2002).

Xiao, et al., "Freeze-Drying of Mononuclear Cells and Whole Blood of Human Cord Blood", CryoLetters, vol. 25, pp. 111-120, (2004).

Avigdor, et al., "CD44 and hyaluronic acid cooperate with SDF-1 in the trafficking of human CD34+stem/progenitor cells to bone marrow", Blood, vol. 103, No. 8, pp. 2981-2989, (2004).

Li, et al., "Morphology Study of Freeze-Drying Mononuclear Cells of Human Cord Blood", CryoLetters, vol. 26, No. 3, pp. 193-200, (2005).

Yu, et al., "Freeze-drying of Human Red Blood Cells: Influence of Carbohydrates and Their Concentrations", Cell Preservation Technology, vol. 2, No. 4, pp. 270-276, (2004).

Thomson, et al., "Isolation of a primate embryonic stem cell line", Proc. Natl. Acad. Sci. USA, vol. 92, pp. 7844-7848, (1995).

Ryan, et al., "Mesenchymal stem cells avoid allogenic rejection", Journal of Inflammation, vol. 2, No. 8, pp. 1 to 11, (2005).

Thomson, et al., "Chapter 4: Primate Embryonic Stem Cells", Current Topics in Developmental Biology, vol. 38, pp. 133-165, (1998).

Rossant, et al., "In Search of the tabula rasa of human cells", Nature Biotechnology, vol. 17, pp. 23-24, (1999).

Wu, et al., "DNA Vaccination Against Specific Pathogenic TCRs Reduces Proteinuria in Active Heymann Nephritis by Inducing Specific Autoantibodies", The Journal of Immunology, vol. 171, pp. 4824-4829, (2003).

Smith, et al., "Gamma irradiation of HIV-1", Journal of Orthopaedic Research, vol. 19, pp. 815-819, (2001).

Huston, et al., "Lack of Efficacy for Conventional Gamma Irradiation of Platelet Concentrates to Abrogate Bacterial Growth", Am J Clin Pathol, vol. 109, pp. 743-747, (1998).

Glaser, et al., "Functional anatomy of articular cartilage under compressive loading Quantitative aspects of global, local and zonal reactions of the collagenous network with respect to the surface integrity", Osteoarthritis and Cartilage, vol. 10, pp. 83-99, (2002).

Danon, et al., "Treatment of Human Ulcers by Application of Macrophages Prepared from a Blood Unit", Experimental Gerontology, vol. 32, No. 6, pp. 633-641, (1997).

"Guidance for Industry: Guidance for Human Somatic Cell Therapy and Gene Therapy", Human Gene Therapy, vol. 12, pp. 303-314, (2001).

Loi, et al., "Development of Parthenogenetic and Cloned Ovine Embryos: Effect of Activation Protocols", Biology of Reproduction, vol. 58, pp. 1177-1187, (1998).

Thomson, et al., "Embryonic Stem Cell Lines Derived from Human Blastocysts", Science, vol. 282, pp. 1145-1147, (1998).

* cited by examiner

SOMATIC CELLS FOR USE IN CELL THERAPY

This is a National Phase Application filed under 35 U.S.C. 371 as a national stage of PCT/IL2006/000902, filed on Aug. 3, 2006, an application claiming the benefit under 35 U.S.C. 119(e) of U.S. Provisional Application No. 60/704,917, filed on Aug. 3, 2005, the content of each of which is hereby incorporated by reference in its entirety.

FIELD OF THE INVENTION

This invention relates to cell therapy and in particular to products and methods for use in somatic cells therapy such as stem cell therapy.

LIST OF REFERENCES

The following references are considered to be pertinent for the purpose of understanding the background of the present invention:
1. WO 03/020874, Improved Method for Freezing Viable Cells;
2. U.S. Pat. No. 5,827,741, Cryopreservation of Human Adult and Fetal Pancreatic Cells and Human Platelets;
3. U.S. Pat. No. 6,723,497, Therapeutic Platelets and Methods;
4. Chen et al. 2001, *Beneficial effect of intracellular trehalose on the membrane integrity of dried mammalian cells*. Cryobiology 43(2):168-81.
5. Crowe et al. 2003, *Stabilization of membranes in human platelets freeze-dried with trehalose*. Chem. Phys. Lipids. 122(1-2):41-52.
6. Fujiki et al. 1999, *Mechanistic Findings of Green Tea as Cancer Preventive for Humans*. Proc. Soc. Exp. Biol. Med. 220(4) 225-228;
7. Kumazawa et al. 2004, *Direct evidence of interaction of a green tea polyphenol, epigallocatechin gallate, with lipid bilayers by solid-state Nuclear Magnetic Resonance*. Biosci Biotechnol Biochem. 68, 1743-7.
8. Suganuma et al. 1999, *Green Tea and Chemprevention* Mutation Research 428, 339-344.
9. Sherry Chow et al. 2001, Cancer Epidemiology, Biomarkers & Prevention 10, 53-58
10. FDA, CBER, 1998, *Guidance for human somatic cell therapy and gene therapy;*
11. US 20050020524, Boyd R L. Hematopoietic stem cell gene therapy
12. U.S. Pat. No. 6,887,704. Peled T, et al. Methods of controlling proliferation and differentiation of stem and progenitor cells
13. US 20050118712, Tsai, M S. Two-stage culture protocol for isolating mesenchymal stem cells from amniotic fluid
14. US 20050042754, Miyazaki J. Induction of the formation of insulin-producing cells via gene transfer of pancreatic beta-cell-associated transcriptional factor
15. US 20050008623, Bechetoille N., et al. In vitro production of dendritic cells from CD14+ monocytes
16. US 20050095228, Fraser J K Methods of using regenerative cells in the treatment of peripheral vascular disease and related disorders
17. US Patent application 20050142118, Wernet P. Human cord blood derived unrestricted somatic stem cells (USSC)
18. US 20050059152, Tanavde V. In vitro culture of mesenchymal stem cells (MSC) and a process for the preparation thereof for therapeutic use
19. US 20040197310, Sanberg P R, et al. Compositions and methods for using umbilical cord progenitor cells in the treatment of myocardial infarction
20. Danon D, Madjar J, Edinov E, Knyszynski A, Brill S, Diamantshtein L, Shinar E. *Treatment of human ulcers by application of macrophages prepared from a blood unit*. Exp Gerontol. 1997 November-December; 32(6):633-41.
21. US 2004191754, Uri M. et. al. Method for Freezing Viable Cells.
22. WO 01/23532, Tsakas S., and Linardos N. Cryopreserved amniotic human cells for future therapeutic, diagnostic, genetic and other uses.
23. YU, J., LIU, J. H., PU, L. Q., CUI, X., WANG, C., OUYANG, S. L., GAO, D. *Freeze-drying of Human Red Blood Cells: Influence of Carbohydrates and Their Concentrations*. Cell Preservation Technology. 2004; 2(4):270-5.
24. U.S. Pat. No. 6,146,890, Danon David. Method and system for cultivating macrophages.
25. Xaio, H. H., Hua, T. C., Li, J., Gu, X. L., Wang, X., W Meng, L. R., Gao, Q. R., Chen, J., Gong, Z. P. (2004) *Freeze-drying of mononuclear cells and whole blood of human cord blood*. Cryoletters; 25(2):111-120.
26. Jun Lil, Tse-Chao Hual, Xue-Lian Gul, Yu Dingl, Ming Luol, Hong-Hai Xiaol, Zhi-Jiang Wu, Lv-Rong Meng, Qi-Rong Gao and Jian Chen; *Morphology study of freeze-drying mononuclear cells of human cord blood*. CiyoLetters 26 (3), 193-200 (2005)
27. Avigdor, A., Goichberg, P., Shivtiel, S., Dar, A., Peled, A., Samira, S., Kollet, O., Hershkovitz, R., Alon, R., Hardan, I., Ben-Hur, H., Naor, D., Nagler, A., Lapidot, T. (2004) *CD44 and hyaluronic acid cooperate with SDF-1 in the trafficking of human CD34+ stem/progenitor cells to bone marrow*. Blood; 103(8):2981-2982.
28. Ptak, G., Clinton, M., Tischner, M., Barboni, B., Mattioli, M., Loi, P. (2002) *Improving delivery and offspring viability of in vitro-produced and cloned sheep embryos*. Biology of Reproduction; 67(6):1719-25.
29. WO 0201952
30. Ryan J. M. et al. (2005) *Mesenchymal stem cells avoid allogeneic rejection*. Journal of Inflammation 2:8;
31. Cord Blood Bank Standard Operating Procedures, Chapter 4, May 1997—Amended July 1999; https://web.emmes.com/study/cord/bld-ch04.pdf

BACKGROUND OF THE INVENTION

Somatic cellular therapy or cell therapy, including gene therapy, already has great importance in medicine. With technological and scientific advancement the role of cell therapy and its possible applications in medicine are likely to increase.

There are currently numerous examples of work being done in the field of cell therapy. One of the most common applications is bone marrow transplantation. In this kind of cell therapy hematopoietic stem cells (HSC) are taken from a donor bone marrow, umbilical cord blood (UCB) or peripheral blood and transfused into a patient. The HSC migrate into the recipient bone marrow where some of the HSC remain as a continuous population of HSC and others differentiate into new and healthy blood cells. This treatment can be autologous, xenogeneic or allogeneic.

Examples of the types of work being done in research in cell therapy include:
  Use of UCB as a source for HSC for treatment of patients whose immune systems have been damaged, such as in US patent application publication No. 2005/0020524, Ex vivo expansion of somatic cells such as in U.S. Pat. No. 6,887,704 and US patent application publication No. 2005/0142118.

The use of somatic cells as study models for the assessment of immunotoxicity/immunotolerance, for the development of cosmetic and pharmaceutical active principles and for the development and implementation of methods of cell and tissue therapy (e.g. US patent application publication Nos. 2005/0118712, 2005/0042754, 2005/0008623, and 2005/0095228).

Culturing mesenchymal stem cells (MSC) and their preparation for therapeutic use such as in US patent application publication No. 2005/0059152. Amongst the published uses for MSC is the grafting of a donor's MSC to a recipient of an organ (from the same donor, in order to prevent graft rejection (immunosuppresion) (Ryan et al., 2005).

Use in treating circulatory disorders and heart problems such as in US patent application publication No. 2004/0197310.

The use of macrophages in wound healing (Danon et al., 1997).

Preservation at a temperature below 0° C. (defined herein as "cryopreservation"), allows for long storage times and may be at any temperature below 0° C., including such temperatures below −20° C., −70° C., −135° C., or in liquid nitrogen. Cryopreservation is achievable by freezing or by vitrification. In vitrification, ice-crystals are not formed, however high concentrations of cryoprotectant agents that are known to be toxic must be added to the biological material. These cryoprotectant agents must be removed before the biological sample is used, in order not to harm the recipient of the biological material. Freezing is also known to cause damage. For example, ice crystals forming in the solution exert extracellular mechanical stress. Intracellular stress can be caused for example by osmosis of water into the extra-cellular space, to replace water that is already frozen.

One factor that has a major effect on the success of cryopreservation is the composition of the solution in which the biological material is immersed prior to freezing. Currently many different cryopreservation solutions are known. Normally, such solutions contain a balanced salt solution such as phosphate buffered saline (PBS), cryoprotectant agents (CPAs), and other molecules including butandiol and methanol.

In addition, sugars, proteins, carbohydrates such as hydroxy ethyl starch (HES), dextran, proteins (especially serum proteins such as albumin) and other macromolecules are also used and are generally termed herein "cryoprotectants". Trehalose, for example, is thought to be protective by binding to lipid polar groups and replacing water. An example for a currently used storage technique may be found in International patent application publication No. WO 01/23532. Currently used cryoprotectant agents, namely, DMSO, ethylene glycol, glycerol and other polyalcohols, are toxic to cells and therefore upon thawing need to be removed or even washed. Use of serum may also be hazardous, since there is a hazard of contamination (especially when the source is human) or if the source is non-human (e.g. bovine) there are also health hazard (e.g. prions and ill match of the cells to the human body).

In most cryopreservation protocols, preservation of the frozen biological material is at a temperature below −130° C. This is normally done in containers of liquid nitrogen (LN) by either immersion of the biological material in LN or in LN vapor. This adds significantly to the cost of long-term preservation. In addition, incidents are known where the LN in the container evaporated (either due to a malfunction of the container or human error) and the biological materials were damaged. Furthermore, when storing in LN cross contamination can occur. This might be discovered only after use and cost also in patients' lives.

Moreover, in many applications, the cell therapy technique includes a step of processing the cells and usually such processed or treated cells are more sensitive to preservation in cold temperatures. The result is that the cells have a very short shelf life after the process is completed and the cells must be administered to a patient (e.g. injected) or otherwise used in a very short time, sometimes even a few hours after the process is completed. This limitation causes the market of providing treated or processed cells to be considered as a "service". A good long term preservation method will allow the treated cells to be regarded more as a "product", ready to be used whenever required and not only when their processing is completed.

One method that can overcome these obstacles is lyophilization of the frozen biological material (e.g. as described in US patent application publication No. 2004-191754). Lyophilization is a process in which ice crystals are removed by sublimation and desorption, resulting in dry, or partially dry, matter. The lyophilized material may be stored at room temperature for a long period of time and be rehydrated for use by simply adding water. Lyophilization results in higher survival rates than air drying or heating, but is still a damaging process.

In order to enhance the biological material's ability to survive the freeze-drying process, intercellular and/or extracellular lyoprotectant agents (LPAs) are often added to the biological material. Carbohydrates and polymers (such as PVP, Dextran, Hydroxy Ethyl Starch (HES), glucose, sucrose, mannose, lactose, trehalose and other) are known to be used for stabilization of the cells during lyophilization and storage in the dry state (Yu et al., 2004).

One method of lyophilization of cells includes introduction of trehalose into the cells. Trehalose is known to protect cell membranes in a dry state (Chen et al., 2001). It was also shown to improve platelet survival after freeze-drying (Crowe et al., 2003).

Umbilical cord blood (UCB) is a source for hematopoietic stem cells (HSC). HSC are cells that can differentiate into all blood cells. Other sources for HSC are bone marrow and a very small amount of HSC can be found circulating in peripheral blood (as WBC). Morphologically, HSC have a round nucleus similar to the mononuclear white blood cells (lymphocytes and monocytes). They resemble lymphocytes very much, and may be slightly bigger. The method to differentiate between them is according to cell membrane antigens. HSC are normally identified by expression of the CD34 antigen. HSC (from peripheral blood, bone marrow or UCB) are given to patients whose immune systems have been damaged, e.g. due to chemotherapy and/or radiotherapy and in different diseases such as: acute and chronic leukemias, myelodysplastic syndromes, Hodgkin lymphoma, non-Hodgkin lymphoma, and multiple myeloma, aplastic anemia, thalassemia, sickle cell anemia, neuroblastoma and more.

The current method for the preservation of somatic cells is using 5-10% DMSO and storage in liquid nitrogen (LN). When storing SC from UCB and from peripheral blood the cells are separated using ficoll-paque and the fraction that is stored are the MNC (Cord Blood Bank Standard Operating Procedures, Chapter 4).

Lyophilization of mononuclear cells derived from human umbilical cord blood was described by Xiao, H. H., et al., 2004 and Lil et al. 2005.

Epigallocatechin Gallate (EGCG)

Epigallocatechin gallate (EGCG) is a polyphenol (MW 458.4) found naturally for example in green and black tea. The well-known beneficial effects associated with such tea are attributed, at least in part, to EGCG. Among the mechanisms associated with EGCG's beneficial effects are its ability to function as an antioxidant, its ability to associate with the phospholipids bi-layer of the cell membrane (Fujiki et al. 1999) and the lipid head groups of liposomes (Kumazawa et al., 2004) and more. Whilst EGCG is the main constituent of green tea, other polyphenols that are found naturally in green tea, such as epicatechin gallate (ECG) epigallocatechin (EGC) and epicatechin (EC), are also found in green tea and, like EGCG, are considered to be non-toxic. These polyphenols share structural and functional properties with EGCG (Suganuma et al. 1999).

International patent application Publication No WO02/01952 describes a preservation fluid for cells and tissues, containing a polyphenol as the active ingredient. The fluid may further contain trehalose.

SUMMARY OF THE INVENTION

The present invention is based on the inventors' surprising discovery that preservation by either freezing or freeze drying of somatic cells, which have either undergone manipulation or not (as described below), and subsequent reconstitution of said cells resulted in viable, functioning post-preservation cells that can be used for the purposes of cell therapy.

The present invention is further based on the finding that preserved mononuclear cells composed mainly of stem cells can be reconstituted and transplanted into an animal, while maintaining their viability and functionality as indicated by their ability to increase the survival rate of immune-compromised animals, and their ability to produce circulating blood cells carrying the graft cell's genetic material.

Thus, the present invention provides, by a first of its aspects, a preserved cell preparation, essentially free of one or more members of a group of cryoprotecing agents consisting of polyalcohols, DMSO and cryoprotecting proteins, the preserved cell preparation comprising somatic cells and at least one polyphenol, wherein upon reconstitution of cells in the cell preparation, at least a portion of said stem cells are viable, said portion being sufficient for use of the cell preparation in somatic cell therapy. Preferably, the cell preparation is free of polyphenol and DMSO and does not require the addition of serum proteins (e.g. albumin, known as a cryoprotecting protein).

In accordance with a second aspect, the present invention provides the use of a preserved cell preparation for the production of a therapeutic composition for somatic cell therapy, the preserved cell preparation being essentially free one or more members of a group of cryoprotecing agents consisting of polyalcohols, DMSO and cryoprotecting proteins, the preserved cell preparation comprising somatic cells, wherein upon reconstitution of cells in the cell preparation, at least a portion of said somatic cells are viable, said portion being sufficient for use of the therapeutic composition in somatic cell therapy.

In accordance with a third aspect, the present invention provides a reconstituted cell preparation being essentially free of one or more members of a group of cryoprotecing agents consisting of polyalcohols, DMSO and cryoprotecting proteins, the preserved cell preparation comprising post-preservation somatic cells and at least one polyphenol, wherein at least a portion of said post-preservation somatic cells are viable, said portion being sufficient for use of the reconstituted cell preparation in somatic cell therapy. According to a preferred embodiment, the reconstituted cell preparation is essentially free of polyalcohol, DMSO and serum proteins (e.g. albumin).

In accordance with a fourth aspect, the present invention provides a method of treating a subject in need of somatic cell transplantation, the method comprises administering to said subject a cell preparation essentially free of one or more members of a group of cryoprotecing agents consisting of polyalcohols, DMSO and cryoprotecting proteins, the preserved cell preparation comprising a effective amount of post-preservation and viable somatic cells the amount of the viable somatic cells being sufficient for re-establishing the stem cells in the subject's body.

In accordance with one embodiment, the somatic cells are stem cells, preferably human stem cells (hSC).

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF THE INVENTION

Figure 1A:
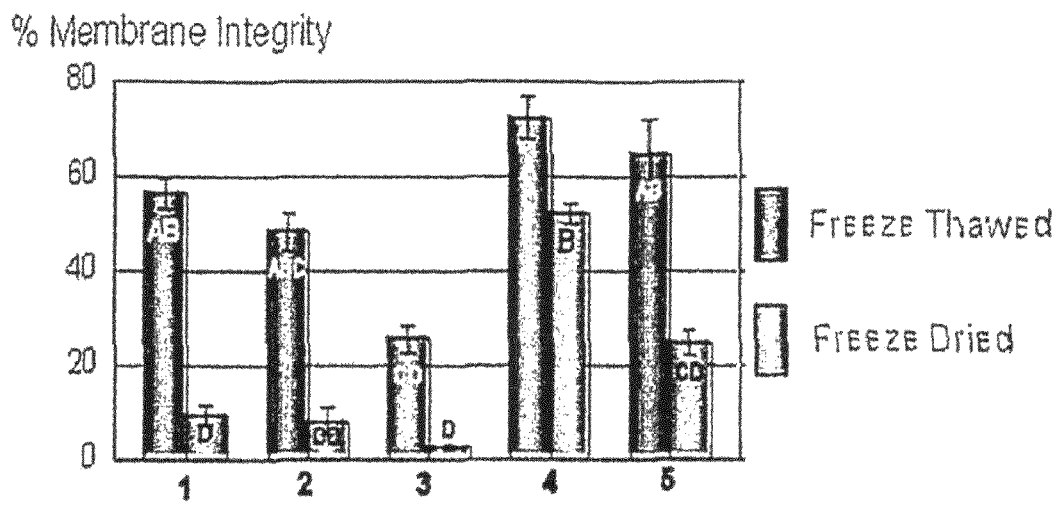
FIGS. 1A-1B are bar graphs showing membrane integrity (FIG. 1A) and percentage (FIG. 1B) of cells after freeze thawing or freeze drying with different solutions: HSA & Trehalose (1) HSA, Trehalose & EGCG (2) HSA & EGCG (3) Trehalose & EGCG (4) Dextran & EGCG (5) (results in FIG. 1A are shown as the percentages of treated samples compared to the fresh samples).

Some terms used herein and their meanings are as follows:

Somatic cells—any sample that comprises cells of an organism, which are not gametes. Such cells include stem cells, white blood cells (WBC), umbilical cord blood (UCB) cells (which are not stem cells) or fractions thereof, embryos, embryonic stem cells, bone marrow cells and other mononuclear cells (MNC), such as lymphocytes or a combination of any of the above. Such cells may be taken from a mammal, e.g. humans.

Stem cells—cells that have the capacity to replicate themselves into cells with similar properties in order to maintain a pool of precursor cells which may then differentiate to produce specialized cell types. Such stem cells may comprise, without limitation, any of the following: pluripotent stem cells, totipotent stem cells, and unipotent stem cells, adult stem cells, embryonic stem cells, hematopoietic stem cells (FISC), mesenchymal stem cells (MSC) and stromal stem cells. HSC may give rise to cells of the lymphoid lineage and to cells of the myeloid lineage. HSC may be obtained from any source, including isolation from mononuclear cells found in Umbilical cord blood (UCB), bone marrow or the peripheral blood. Such cells may be taken from a mammal, e.g. humans and human derived stems cells.

Cellular therapy or cell therapy—administration to humans of autologous, allogeneic, or xenogeneic living cells for any purpose including diagnostic or preventive purposes (Guidance for Industry-Guidance for Human Somatic Cell Therapy and Gene Therapy, FDA, Center for Biologics Evaluation and Research (CBER), March 1998), and healing or treatment of any condition or malady, for example regenerative medicine.

For the purpose of this invention, the term cell therapy also includes the process of therapeutic cloning which means the use of stem cells to produce cloned embryo that serves as a source for embryonic stem cells used for cell therapy. In the framework of cellular therapy use may be made of any appropriate somatic cells as known in the art, including but not necessarily manipulated cells. Cellular therapy may also include the use of stem cells for production of tissue or organ for transplantation including the use of the cells for therapeutic cloning (e.g. as a source for nuclei in nuclear transfer).

Regenerative medicine—any technique to replace or repair organs or tissues that are damaged by disease, aging or trauma, so that function can be restored or at least improved by means other than transplantation of the same intact tissue or organ. (http://www.chemeng.mcmaster.ca/courses/che4t3/Regenerative %20Medicine4.pdf). This includes the use of scaffolds, cell selection, genetic engineering and tissue engineering methods. It encompasses, among other things, the fields of tissue engineering, biomaterials, and stem cell applications.

Manipulated cells—somatic cells (e.g. stem cells) that underwent any treatment, processing or manipulation, for any purpose other than manipulation that is related solely for the preservation of the cells (such as addition of a preservation agent or solution, cooling, lyophilizing etc.). Examples for such manipulated cells include cells that underwent one or more of: separation (from other cells or materials), expansion, culturing, mixture with other material (e.g. biological or chemical), activation, differentiation etc. and any other treatment that is intended to allow the cells to be used for cell therapy. Manufacture of products for stem cell therapy may involves the ex vivo propagation, expansion, differentiation, selection or pharmacologic treatment of cells, or other alteration of their biological characteristics.

Preservation—the process of maintaining cells under conditions in which its biological activity is considerably reduced (or eliminated) while it nonetheless remains viable and may resume essentially normal biological activity when taken out of the preservation state. Specific examples of preservation are hypothermic preservation and cryopreservation (including e.g. freezing and freeze drying).

"Preserved cells"—cells maintained under conditions in which their biological activity is considerably reduced (or eliminated) while they nonetheless remain viable and may resume essentially normal biological activity when taken out of the preservation state. The cells may be preserved by any known preservation method, including those mentioned above.

Preservation solution—a solution permitting the preservation of biological material, such that it retains its viability. A specific embodiment of a preservation solution is one for preserving biological material at low temperature. Such solution comprises such components that would allow the biological material to endure the preservation and, at times, also sustain the biological material, while being preserved. It would normally comprise a balanced salt solution such as phosphate buffered saline (PBS) or Sodium Chloride (NaCl) and other constituents that are known to improve the biological material's ability to withstand preservation conditions. Hypothermic preservation solutions and cryopreservation solutions are examples of preservation solutions.

Cryopreservation—a process including at least one step of lowering the temperature of biological material from a temperature that is above the freezing temperature of the biological material (or the solution in which it is immersed) to a temperature that is below that freezing temperature. Cryopreservation encompasses freezing, vitrification and lyophilization. The term "cryopreservation solution" refers to any solution or media in which a biological material is immersed before cryopreservation. Typically, cryopreservation solutions contain a balanced salt solution such as phosphate buffered saline (PBS) or NaCl and at least one (intracellular and/or extra-cellular) cryoprotectant agent (CPA) or intracellular and/or extra-cellular lyoprotectant agent (LPA) or polyalcohol. A cryopreservation solution may be a freezing solution, a vitrification solution, a lyophilization solution and/or a mixture of such solutions.

Freezing—a process of cryopreservation that causes the formation of ice crystals within the frozen material.

Appropriate freezing conditions—freezing conditions that would maintain cells of a biological material in a viable state. Such conditions relate to the freezing solution and its constituents (e.g. a freezing solution with added polyphenols that optionally does not comprise a significant amount of a polyalcohol, CPA and/or glycerol and/or DMSO and/or other undesired chemicals such as ethylene glycol, propylene glycol and other alcohols, butandiol and methanol), the freezing protocol including rate of cooling, temperature regime, directional freezing or stationary freezing, and the like. Non-limiting embodiments for such appropriate conditions include those embodiments and examples described herein.

Freezing solution—any solution or media in which biological material is immersed before freezing. It comprises constituents that are intended to maintain the biological material whilst reducing the damage caused to the biological material by freezing and/or thawing. Freezing solutions normally comprise intercellular and/or extra-cellular CPAs.

Lyophilization or freeze-drying—a process of cryopreservation in which cells are frozen and afterwards at least partially dried. Thus, in the present invention wherever cells are said to be freeze-dried or lyophilized, this may mean that at least two steps were executed, one of which for freezing the material and the other for at least partial drying.

Lyophilization solution—any solution or media in which a biological material is immersed before lyophilization. Typically, lyophilization solutions contain constituents that are intended to maintain the biological material whilst reducing the damage caused to the biological material by freezing, drying, during storage and/or re-hydrating. Lyophilization solutions normally comprise one or more intercellular and/or extra-cellular LPAs. Lyophilization normally begins as primary drying (wherein water content of the biological material is reduced by 90-95%) and then secondary drying (wherein water content is reduced below 90-95%).

Cryoprotectant agent—any agent that is added to a solution and which improves the post thaw viability of a biological material cryopreserved in that solution. Intracellular CPAs are thought to replace water inside the cells, thus preventing crystallization therein, to enlarge the un-frozen fraction of the frozen solution, to buffer osmolarity and/or to stabilize the membrane and prevent mechanical damage caused by ice crystals. Examples of CPAs are DMSO, glycerol, ethylene glycol, poly ethylene glycol (PEG), propylene glycol, sugars, such as sucrose, dextrose, trehalose, and proteins (e.g. serum proteins, albumin, fetal calf serum, of human or other source, etc), carbohydrates such as hydroxy ethyl starch (HES), dextran, etc.

Lyoprotectant agent—a substance that is added to a solution and stabilizes biological material during lyophilization in said solution and/or during storage and may result in higher viability rates. Examples of LPAs include antioxidants, sugars, membrane stabilizers, high molecular weight molecules, etc.

Essentially free of [material]—free of the stated material (e.g. any polyalcohols such as glycerol, or DMSO, or serum proteins or any other serum components), or that any amount of the stated material present in the solution is so low so as not to have any effect (or at least no significant effect) on the preservation process, on the outcome of the preservation process or on the properties of the biological material (for example the viability of living matter, e.g. cells, if such are included in such material) after it is taken out of the preservation conditions.

Appropriate storing conditions—any such conditions that maintain the somatic cells viable. Under such conditions the temperature may be any temperature above 0° C. (e.g. room temperature) or below 0° C., as long as, the cells are kept away from humidity and oxygen (e.g. under vacuum or with an inert gas displacing all air, such as Nitrogen, Argon, etc.). Generally, dryer lyophilized cells may be maintained at higher temperatures with minimal damage than cells that are less dry. In addition, the nature of the components of the lyophilization solution affects the storage temperature, since storage is best if it is at such temperature where the components of the solution do not liquefy. It is appreciated that when the somatic cells are lyophilized and intended to be stored at a given temperature (e.g. room temperature), it is preferred that the preservation solution will not contain agents (e.g. cryoprotectant agents or lyoprotectant agents) that are liquid at the given temperature. Finally, it is recommended that storage be away from light and any other form of radiation (at all temperatures).

Polyphenol(s)—both natural and/or synthetic polyphenol. Examples include catechins, such as those naturally found in green tea. Examples of catechins are epigallocatechin gallate (EGCG), epicatechin gallate (ECG) epigallocatechin (EGC) epicatechin (EC), DL-Catechin (DL-C) gallocatechin gallate (GCG), and including any other catechin, natural or synthetic and any mixture thereof. The term "polyphenols" also denotes, without limitation, green tea extract (GTE) that comprises catechins as well as any catechin-comprising fraction thereof. Smaller amounts of catechins are also found in other sources such as black tea, grapes and wine. When biological material is claimed in the context of this invention as comprising polyphenols, the amount of polyphenols is in excess of the amount naturally found in the relevant biological material.

Viable—cells that are functional or capable of functioning as measurable by any one of a variety of assays and models known in the art. Cells that, in their majority are said to have survived cryopreservation, are considered viable cells. The term viable may be used to describe cells that are capable of cell therapy, for example, stem cells (e.g. HSC) that are able to proliferate and re-establish a function (e.g. the immune system) of an animal or human. Additionally, in vitro assays may be used to evaluate the functional recovery of the cells, for example, a colony forming unit (CFU) assay that evaluates the ability of the stem cells to from colonies, or a proliferation assay. In addition membrane integrity assay can be used, a metabolism assay or even a simple cell counting assay. Numerous such assays are known in the art including such assays as described in the experiments section of this application. In some cases, the actual and desirable function of the cell is not required in vivo, for example when the cells are used in therapeutic cloning; in such cases the functional recovery of the cell is being measured by the outcome of the in vitro procedure, for example, development of embryos using somatic cells cloning. Therefore, the term viable can also refer to somatic cells that are capable of being used in cloning as part of a therapeutic cloning process. In some preferred embodiments viable cells are cells, which have at least 50% viability or even at least 60% viability as compared to fresh cells, which may be assayed for example using membrane integrity as an indication of viability.

Reconstituted cells—Cells after preservation, particularly after cryopreservation, and which were taken out from the preservation state, i.e. were brought to their original consistency by thawing, warming, rehydrating and the like of the preserved cells.

Establishment of cells—reconstituted cells which exhibit a similar functionality to that of the original cells prior to preservation.

Washing—a process wherein cells are removed from a solution in which they are immersed and suspended in a new solution at least once, twice or more.

The present invention is based, among other things, on the inventors finding that EGCG protects mononuclear cells (and especially stem cells) during preservation processes including cooling, cycles of freezing and thawing, freeze-drying and hydrating and that these preserved cells were capable of re-establishing the immune system in an immune compromised animal after transplantation. It has then been envisaged by the inventors that with the ongoing progresses in the field of cell therapy, a need exists for providing preserved somatic cell preparations. Thus, the present invention is aimed at providing preserved somatic cell preparations (preferably stem cells) particularly for use in cell therapy, such as stem cell transplantation.

One of the benefits of using EGCG is that this compound, and to a lesser extent the other polyphenols, are considered beneficial food additives and as such may not need to be removed from the biological material before the biological material is used. In fact, the FDA classified EGCG as GRAS (Generally Regarded As Safe).

The present invention particularly concerns somatic cells. A non-limiting and preferred group of somatic cells in accordance with the invention include stem cell. Examples of stem cells in accordance with the invention non-exclusively include hematopoietic stem cells (HSC) obtained from bone marrow tissue of an individual at any age or from cord blood of a newborn individual, embryonic stem cells (ESC)

obtained from the embryonic tissue formed after gestation (e.g., blastocyst), or embryonic germ cells (EGC) obtained from the genital tissue of a fetus any time during gestation, preferably before 10 weeks of gestation and mesenchymal stem cells (MSC). Preferred stem cells according to the present invention are human stem cells, more preferably, HSC and MSC. According to some embodiments of the invention, the stem cells comprise or consist only of non-embryonic stem cells. According to yet other embodiments of the invention the somatic cells do not consist of stem cells.

Somatic cells can be obtained using well-known cell-culture methods. For example, hESC can be isolated from human blastocysts. Human blastocysts are typically obtained from human in vivo pre-implantation embryos or from in vitro fertilized (IVF) embryos. Other options for obtaining embryonic stem cells include use of somatic cells as donors for nuclear transfer. The nucleus is transferred into an enucleated oocyte and resulting in an embryo having the donor's genes. Yet another option is the formation parthenogenetic embryos (where oocytes are chemically activated to form an embryo). Alternatively, a single cell human embryo can be expanded to the blastocyst stage. For the isolation of human ESC the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation, or by an enzymatic degradation, and the cells are then re-plated on a fresh tissue culture medium. Colonies demonstrating undifferentiated morphology are individually selected by micropipette, mechanically dissociated into clumps, and re-plated. Resulting ESC are then routinely split every 1-2 weeks. For further details on methods of preparation hESC see Thomson et al., [U.S. Pat. No. 5,843,780; Science 282:1145, 1998; Curr. Top. Dev. Biol. 38:133, 1998; Proc. Natl. Acad. Sci. USA 92: 7844, 1995]; as well as Bongso et al., [Hum Reprod 4: 706, 1989]; and Gardner et al., [Fertil. Steril. 69:84, 1998].

Commercially available somatic cells can also be used in accordance with the invention. Stem cells, such as Human ESC, may be purchased for example from the NIH human embryonic stem cells registry. Non-limiting examples of commercially available embryonic stem cell lines are BG01, BG02, BG03, BG04, CY12, CY30, CY92, CY10, TE03 and TE32.

Potential applications of somatic cells (e.g. hESC) are far ranging and include drug discovery and testing, generation of cells, tissues and organs for use in transplantation, production of biomolecules, testing the toxicity and/or teratogenicity of compounds and facilitating the study of developmental and other biological processes. For example, diseases presently expected to be treatable by therapeutic transplantation of hESC or hESC derived cells include Parkinson's disease, cardiac infarcts, juvenile-onset diabetes mellitus, and leukemia [Gearhart J. *Science* 282: 1061-1062, 1998; Rossant and Nagy, *Nature Biotech.* 17: 23-24, 1999].

In some embodiments of the invention, small amounts of one or more polyalcohols, e.g. glycerol, or other CPAs (e.g. DMSO or serum proteins) that are conventionally used in preservation of biological material, particularly in preservation procedures involving cooling to below freezing, may be included in the preservation solution. However, it was surprisingly found that it is possible to preserve cell preparations mainly comprising stem cells even without use of any one of polyalcohols, DMSO and serum in the preservation solution. The preservation solution used in accordance with the invention is thus preferably essentially free of any such CPA additives.

The preserved cell preparation of the present invention may be obtained by hypothermic preservation or by cryopreservation, including freezing, lyophilization (freeze-drying), and combinations of same.

The cells for preservation may be obtained from any source of somatic cells, e.g. mononuclear cells (MNC), umbilical cord blood cells (UCB), hematopoietic stem cells (HSC) and bone marrow, adipose tissue.

The appropriate storing conditions for the preserved cell preparation of the present invention comprise any such conditions that maintain the cells viable. Such conditions normally include the temperature, which in the case of frozen samples must be below 0° C., preferably below −20°, below −70° C., below −80° C., below −135° C., or below −190° C. (e.g. in LN). The following non-limiting examples show that preservation in a mechanical freezer at a sub-zero temperature above −100° C. (preferably below −70° C., or between −75° C. and −85° C.) overnight, and at even lower temperature (in LN) for over 8 days resulted in viable reconstituted cells. Further, the following non-limiting examples show that lyophilized cells may be preserved for months (even 18 months and longer in room temperature) and provide thereafter viable reconstituted cells. Thus, there is clear evidence that the preserving somatic cells in accordance with the invention can be used for long term preservation of the cells without causing significant damage to the cell population once reconstituted (taken out from the preservation conditions).

In case of hypothermic preservation, the temperature is normally between 8° C. and 0° C. In the case of lyophilized samples, the temperature may be any temperature above 0° C. (e.g. room temperature) or below 0° C., as long as, the material is kept away from humidity and oxygen. Generally, dryer lyophilized cells may be maintained at higher temperatures with minimal damage than material that is less dry. In addition, the components of the lyophilization solution affect the storage temperature, since storage is best if it is at such temperature when the components of the solution do not liquefy. It is appreciated that when the cells are lyophilized and intended to be stored at a given temperature (e.g. room temperature), it is preferred that the preservation solution will not contain agents (e.g. CPAs or LPAs) that are liquid at the given temperature. Finally, it is recommended that storage be away from light and any other form of radiation (at all temperatures).

A person skilled in the art of the invention would appreciate that the adding of the preservation solution may be done in one or more steps such that one or more of the solutions' components would be added separately. Preferably, but not necessarily, the preservation solutions would not contain substances that would need to be removed from the cell preparation prior to use.

According to one embodiment, the preserved cell preparation is obtained by freezing of the cells at a cooling rate of 5.1° C./min. until the cells are frozen.

According to another embodiment, the preserved cell preparation is obtained by freezing of the cells at a cooling rate of 5.1° C./min. until the cells are frozen followed by freeze-drying of the frozen cells.

It is noted that the invention concerns small as well as large volumes (e.g. 50 ml) of cell preparation. This is evident from the following examples relating to large volumes of samples (30 ml and 50 ml). This result is surprising, for example, since with large volume of cell samples the risk of prolonged recrystallization is greater, and thus there is a greater probability of causing damage to the cells within the cell preparation. As appreciated, the larger volume of the cell preparation means a greater amount of bulk in the sample. Heat removal across the bulk of the sample is required which limits the rate of cooling.

The polyphenols used in the preparation of the preserved cells of the present invention may include one or more catechins, such as EGCG, or be provided as green tea extract (GTE). EGCG may be added for example at any concentration up to 1M, preferably between about 50 μM and about 4 mM. One of the benefits of the present invention is that additives that are known to be hazardous or toxic, such as glycerol, other polyalcohols, DMSO, proteins or any other undesired chemicals conventionally used in preservation of biological material, need not be added.

A person skilled in the art of the invention would be able to adjust the contents of the preservation solution to the duration and purpose of preservation and the type of biological material to be preserved. For example, when the purpose is hypothermic preservation, the preservation solution is a hypothermic preservation solution. When the preservation is cryopreservation, the preservation solution is a cryopreservation solution. In such case the solution may be for example a freezing solution (in which case the biological material is frozen) or a lyophilization solution (in which case the biological material is lyophilized). Likewise, any physiologically acceptable buffer or salt may be used in addition to or instead of PBS or NaCl. Non-limiting examples of such buffers are Hepes Talp, RPMI-1640 and F-12. Examples of additional ingredients that may be used in the solution are macromolecules that may protect the cells from mechanical damage, such as sugar, including dextran (for example, 20%-30%). A preferred additive is trehalose and a preferred concentration thereof is 0.1M. Thus, in accordance with one preferred embodiment of the invention the preserved cell preparation comprises a combination of EGCG and trehalose (0.1M).

Preferably, the preservation solutions would not contain substances that would need to be removed from the biological material prior to its use. It is also preferable that the preservation solution would contain only elements that are considered safe or are known to be found in blood without known hazardous effects. For example, EGCG was found circulating in blood of human subjects after consumption of green tea (Sherry Chow et al. 2001).

One of the benefits of the present invention is that the preserved somatic cells may be essentially free of additives that are known to be hazardous or toxic, such DMSO or polyalcohols such as glycerol, or serum proteins and other undesired chemicals such as ethylene glycol, propylene glycol and other alcohols, butandiol and methanol). The term "essentially free" more specifically defines that the additives in the cell preparation are less than 5%, preferably less than 3%. The preserved cell preparation of the present invention may comprise stem cells selected from MNC, UCB, and HSC, MSC (mesenchymal stem cells), and may have any temperature, above or below zero including temperatures of cryopreservation or room temperature, providing that the cells are viable. In addition, the cell preparation may be in a dry state or almost fully dry (comprising 20% or less or even 0.10% or less of its original water content).

The preserved cell preparation of this invention may accordingly be provided in a hypothermic, frozen or freeze-dried state. It may also be provided in a revived/reconstituted and viable form, after having been warmed, thawed and/or hydrated using any method known in the art that is compatible with the type and condition of the preserved cells.

Freeze-drying and cryopreservation in accordance with the present invention may be carried out in any method suitable to the cells in question. The freezing step of the above methods of the present invention can be done in any method or apparatus known in the art. A preferred example would be using a directional freezing device such as that which is described in US patent application publication No. 2006/0057555 (derived from WO 03/020874), incorporated herein by reference in its entirety. Nevertheless, any freezing method which allows cryopreservation of cells may be used, including using mechanical freezers, stepwise freezing apparatus, the Planner freezing apparatus, slush freezing, freezing in cryogenic fluid, freezing in controlled rate freezers, liquid bath freezer or cold air freezers, etc. Likewise, the biological material may be treated additionally in one or more methods known in the art, such as those described in U.S. Pat. No. 5,827,741 or U.S. Pat. No. 6,723,497, incorporated herein by reference in their entirety.

The invention also provides the use of a preserved cell preparation for the production of a therapeutic composition for stem cell therapy, the preserved cell preparation being essentially free of polyalcohols and comprising stem cells, wherein upon reconstitution of cells in the cell preparation, at least a portion of said stem cells are viable, said portion being sufficient for use of the therapeutic composition in stem cell therapy.

The preserved cell preparation may be used in combination with at least one physiologically acceptable additive suitable for transplantation of said cell preparation in a mammalian subject. A non-limiting list of additives acceptable for stem cell therapy is provided in Cord Blood Bank Standard Operating Procedures, Chapter 4, May 1997 Amended July 1999.

The present invention also provides a reconstituted cell preparation being essentially free of polyalcohol and comprising post-preservation stem cells and at least one polyphenol, wherein at least a portion of said post-preservation stem cells are viable, said portion being sufficient for use of the reconstituted cell preparation in stem cell therapy.

In fact, the preserved cell preparation may also be further manipulated in order to prepare the final form of a therapeutic composition including the reconstituted cells that would eventually be administered to a subject in need of stem cells. The therapeutic composition would comprise the reconstituted cell preparation or cells that were derived from the stem cells of the cell preparation, e.g. their progeny, or cells comprising a significant portion of said stem cells (e.g. the nucleus).

Reconstitution of the cells in the cell preparation may be achieved by any method known for reconstitution of preserved biological material, including, without being limited thereto, controlled warming, thawing and/or re-hydrating said cells.

According to one embodiment, a portion of the stem cells in the reconstituted cell preparation after being taken out from the preservation condition are viable. Preferably at least 20%, 40% or at least 70% of said cells are viable after freeze drying of the cells and at least 80% or at least 90% of the cells are viable after freezing of the cells.

Viability may be assayed by any known method, such as a membrane integrity assay. Due to the toxic effects known to be associated with polyalcohols, such as glycerol, and DMSO, and due to the hazardous nature of serum components or proteins, it is preferred that the reconstituted cell preparation would not comprise a significant amount thereof.

Preferably, the reconstituted cell preparation comprises a polyphenol, for example epigallocatechin gallate (EGCG).

The invention also provides a method of treating a subject in need of cell (preferably stem cell) therapy, the method comprises administering to said subject a cell preparation reconstituted from preservation conditions, the cell preparation being essentially free of polyalcohol and comprising a effective amount of post-preservation and viable somatic cells the amount of the viable somatic cells being sufficient for re-establishing the somatic cells in the subject's body.

In accordance with one embodiment, the method comprises administering to said subject a cell preparation reconstituted from preservation conditions and is essentially free of polyalcohol as well as of DMSO.

The method of the invention is applicable for autologous, allogeneic as well as xenogeneic cell transplantation. However autologous and allogeneic stem cell transplantations are preferred as these therapies are clinically approved.

Patients typically undergo a pre-transplant workup to evaluate, for example, heart, liver, kidney, and lung function, as well as current disease status. In some embodiments, patients deemed, to be eligible (e.g., healthy enough) for autologous stem cell transplantation (ASCT) are subjected to a tumor de-bulking procedure prior to ASCT. For example, a patient can be treated with high doses of chemotherapy, radiation therapy, and/or surgery (e.g., surgery with anesthesia) before the transplant. Stem cells for transplant typically are collected prior to tumor de-bulking regimens, since such potentially lethal procedures can be immunosuppressive and can severely damage or destroy the bone marrow. ASCT following a de-bulking procedure can reconstitute the patient's immune cells with stem cells present in the transplant. In some other embodiments, a patient's stem cells can be collected by bone marrow harvest using procedures known in the art, or by a stem cell apheresis procedure. Collected stem cells can then be cryopreserved in accordance with the invention, and the patient can undergo a de-bulking procedure such as high-dose chemotherapy and/or radiation therapy. After the debulking procedure is completed, the patient's stem cells can be reconstituted and transplanted. ASCT can be done almost immediately after a de-bulking procedure (e.g., 24 to 48 hours after HDT), however, in accordance with the invention, when a longer period of time (e.g., a week to several months) can elapse between a de-bulking procedure and ASCT, the cells are preserved. Due to the likelihood of immuno-suppression as a result of the de-bulking procedure, protective isolation precautions generally are taken after ASCT at least until the re-infused stem cells begin to engraft. "Engraftment" refers to a process whereby the transplanted stem cells begin to differentiate into mature blood cells. In addition, stem cells can be treated prior to transplantation with, for example, anticancer drugs or antibodies to reduce the number of cancerous cells that may be present in the sample. Such procedures are referred to as "purging".

The reconstituted somatic cells may be combined with agents suitable for cell transplantation, such as agents which improve the engraftment, including fresh or reconstituted MSC, and immunosuppressive drugs such as Cyclosporines, Tacrolimus, and Sirolimus.

Additionally, the preserved cell preparation of the present invention may be part of a stem cell transplantation kit, comprising in addition to the preserved cell preparation of the present invention instructions for reconstituting the preserved cell preparation. Such instructions may relate to one or more of the manner of warming, thawing or hydrating the preparation, manipulating the cell preparation after its reconstitution, the method of administration of the reconstituted cell preparation, the term during which the reconstituted cell preparation may be used, details regarding the suitable storage conditions for the preserved as well as the reconstituted cell preparation, etc.

Finally, when using a lyophilized, i.e. dry (or essentially dry) cell preparation of the present invention may be used as a component in a biosensor or bioreactor or in the operating thereof. A biosensor is a device comprising a biological component (e.g. microorganisms, tissue, cells portions of cells, enzymes, antibodies, nucleic acids etc), for the detection of an analyte. The device also comprises a detector component (e.g. physicochemical, electrochemical, optical etc.). Amongst the known commercially available biosensors are blood glucose biosensors. Other known applications of biosensor include the detection of toxic substances, for example in environmental monitoring and in water treatment facilities. The present invention provides for the first time, a dry cell composition for use in a biosensor. A biosensor comprising dried cells composition of the present invention may be stored even at room temperature for a relatively long period of time (e.g. days, weeks, months or even years). An additional benefit of the biosensor of the present invention is in that a single step may be used for activation of the cells and operation of the biosensor (e.g. when assaying water, the assay sample may be used in the re-hydration of the cells).

A bioreactor is an apparatus that maintains a biologically active composition (e.g. a cell suspension or tissue culture). A bioreactor may be limited for grow cells or tissues or for the production of substances facilitated by the biological material. The bioreactor is capable of maintaining and carefully monitoring predefined environmental conditions, including temperature, humidity, pH, gas composition (i.e., air, oxygen, nitrogen, $CO_2$) and dissolved oxygen levels, flow, circulation rate, etc. In addition, the bioreactor should be capable of removing waste and introducing fresh nutrients and the like, and optionally replace dead/aged cells. Bioreactors are normally controlled in an automated computerized fashion. A unique bioreactor was developed by NASA, for artificially growing tissue (e.g. heart tissue, skeletal tissue, ligaments, cancer tissue) in Cell cultures.

A bioreactor comprising dried cells preparation of the present invention may be stored (or transported) at room temperature (or through cold outer-space) for a relatively long period of time (e.g. days, weeks, months or even years). An additional benefit of the bioreactor according to the present invention is in that it may be fully automated with respect to the step of adding fresh cells, wherein in a single step dry cells are added into the medium within the reactor (or before addition of the medium to the reactor).

NON-LIMITING SPECIFIC EMBODIMENTS

In the following some non-limiting examples are provided, showing how the present invention may be practiced.

Materials and Methods

Unless otherwise stated, all materials were purchased from Sigma Inc. (St. Louis. Missouri, USA) and PBS means phosphate buffered saline ($Ca^{+2}$ & $Mg^{+2}$ free).

Preparation of Umbilical Cord Blood (UCB) Cells

In the following experiments umbilical cord blood (UCB) was received from "Sheba" Medical Center. The blood was separated on ficoll-paque gradient. 3 ml of Histopaque 1077 was put in a 15 ml plastic test tube. Above it 3 ml of UCB was put and the samples were centrifuged for 30 minutes at 1000 g. After spinning was finished the mononuclear layer was taken out and PBS was added up to 10 ml total volume. The samples were centrifuged again for 10 minutes at 200 g or 250 g., after which, the supernatant was discarded and another step of washing was performed (again, 10 ml PBS was added and samples were centrifuged for 10 minutes at 250 g). At the end of this step a freezing solution (as detailed in each experiment) was added to the cells pellet. The volume of the freezing solution varied depending on the desired cell concentration (concentrations may range for example from 1 to $10 \times 10^6$ cells/ml) or volume. Unless otherwise mentioned, a 2.5 ml cell suspension was transferred into a 16 mm glass tube that was then frozen using a multi-gradient directional freezing system (MTG-516 by IMT, Israel), operated essentially as described in WO03/020874.

Freezing Procedures

Unless otherwise stated, the directional freezing system temperatures were set to: 5° C. to −10° C. to −40° C. to −70° C. Seeding was performed before the samples entered the −10° C. temperature. The velocity at which the samples were pushed through the channels of the freezing machine was set to 0.2 mm/sec, resulting in a cooling rate of 5.1° C./min. During freezing the samples were rotated at 60 rounds per minute (RPM). After completion of the freezing process, samples were put in a liquid-nitrogen (LN) tank until they were either thawed or transferred into a lyophilizer.

In all of the following experiments, freezing was done using this protocol, unless stated otherwise. Thawing was done by immersing the samples in a water bath at 37° C.

Lyophilization Procedure

Lyophilization was performed by taking samples out of the LN tank and putting them in a commercial lyophilizer near the condenser (Labconco, USA), at condenser temperature of −80° C. Samples were held in the lyophilizer for 3 days. After 3 days of lyophilization samples were taken out and rehydrated with 2.4 ml of double distilled water (DDW) at 37° C.

Viability Determination

Viability was assessed using the live/dead fluorescent stain SYBR14/PI (Propidium Iodide) or SYTO/PI (both from Molecular Probes, USA) for membrane integrity. These stains are nucleic acid stains, SYBR14 and SYTO are membrane permeable molecules and PI can enter the cell only if the membrane is damaged. Where so specified, the assay used was trypan blue (TB).

Cell Metabolism

Cell metabolism was assessed using the cell proliferation kit (Biological Industries, Israel). This is a colorimetric assay which is based on the activity of mitochondrial enzymes and uses the tetrazolium salt XTT. Cells are cultivated in a flat 96-well plate. To each well we added 100 μl growth medium consisting of: RPMI 1640 supplemented with 100 fetal calf serum and 1% 200 mM L-glutamine, 100 units/ml penicillin and 100 μg/ml streptomycin. In each well we had 2.5-5*106 cells/ml. After being incubated for 3 hours, samples were read in an ELISA reader (Bio-Tek Instruments, USA) at a wave length of 450-500 nm.

Cells Recovery

Cells recovery was evaluated by cells counts that were performed before and after treatments using the automatic cell counter Pentra 60 (ABX Diagnostics, France).

Statistics

At least three replications for each experiment were performed (i.e. blood from 3 donors). From each sample at least 300 cells were counted. Means were calculated and differences between treatments examined by t-tests using the General Linear Model procedure of JMP (SAS Institute, 1994). Significance was $P<0.05$ unless otherwise stated. Different letters represent statistically different samples. Results are shown as the calculated means and their standard deviations.

Results

Mononuclear Cells (MNC) Derived from Umbilical Cord Blood (UCB)

In the following experiments, all cell samples contained mononuclear cells obtained from UCB.

Experiment A:

Mononuclear cells obtained from UCB were subjected to freezing and freeze drying with different freezing solutions as follows:
1) 0.1M Trehalose, 12.5% (w/v) human serum albumin (HSA) in PBS.
2) 12.5% (w/v) HSA and 0.1M Trehalose and 0.189 mg/ml EGCG in PBS.
3) 12.5% (w/v) HSA with 0.189 mg/ml EGCG in PBS.
4) 0.189 mg/ml EGCG with 0.1M trehalose in PBS.
5) 30% (w/v) Dextran with 0.189 mg/ml epigallocatechin gallate (EGCG) in PBS.

FIG. 1A shows the viability rates as demonstrated by membrane integrity of the cells. Specifically, it is shown that the solutions composed of EGCG and trehalose or EGCG and Dextran gave best results after freezing and thawing or freeze drying and then re-hydration.

Figure 1B:
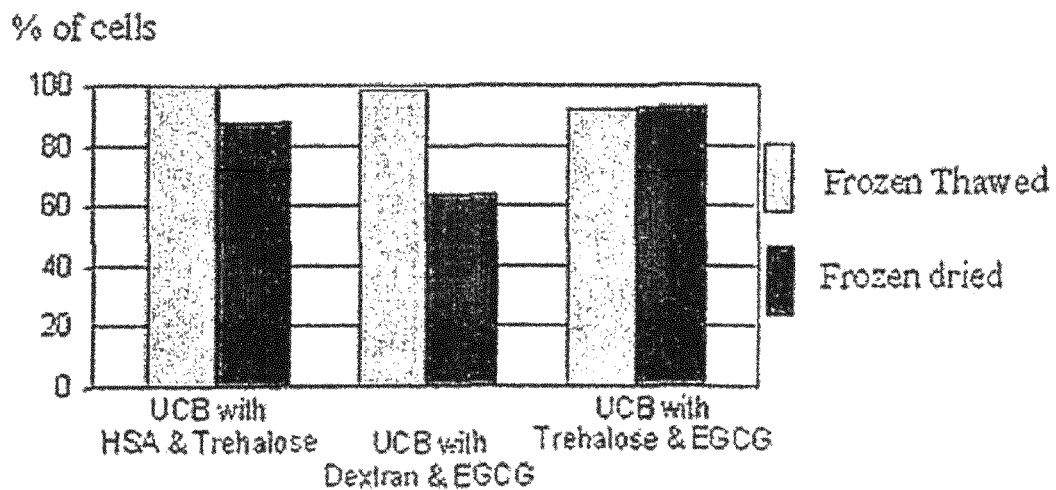

FIG. 1B presents the percentage of the total number of cells (as counted using the Pentra 60 (ABX, France)) that showed the best results in FIG. 1A (referred to as solution number 1, 4 and 5). As appreciated, membrane integrity is a parameter for cell viability. With trehalose and EGCG most of the cells recover resulting in recovery rates of 92.06% after freeze thawing and 93.18% after freeze drying, whereas, after freeze drying with dextran and EGCG only 64.36% of the cells survived and after freeze drying with HSA and trehalose 87.66% of the cells recovered. With all three solutions after freeze thawing more then 90% of the cells survived, with 100% recovery of samples frozen with HSA and trehalose, 98% recovery with samples frozen with dextran and EGCG and 92% with the samples frozen with trehalose and EGCG.

Experiment B1:

The effect of different EGCG concentrations in a solution comprising EGCG and trehalose was evaluated. The solutions were composed of 0.4M Trehalose and one of the following EGCG concentrations: 0.189, 0.47, 0.945 and 1.89 mg/ml EGCG, all in PBS. As a control a solution composed of 0.4M trehalose and 12.5% (w/v) human serum albumin (HSA) was used. All other experimental steps were performed as described above.

Figure 2A:
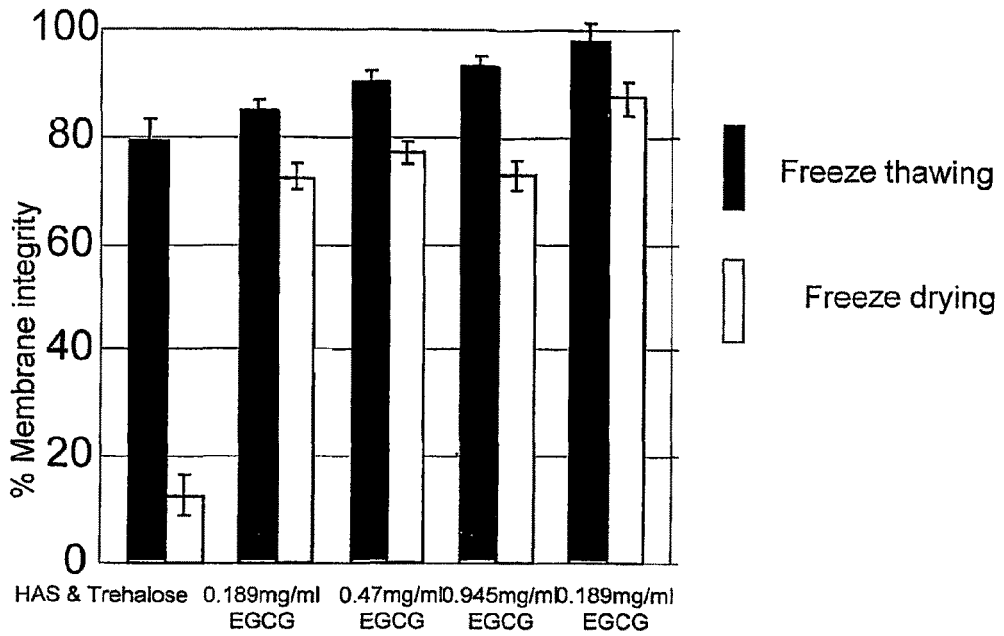
FIGS. 2A-2B are bar graphs demonstrating the percent of membrane integrity of samples after freeze thawing and freeze drying as compared to the fresh samples (set as a 100%) using a freezing solution comprising 0.4M trehalose (FIG. 2A) or 0.1M trehalose (FIG. 2B). The graphs show an EGCG dose response on UCB derived MNC.

FIG. 2A shows that viability increased with increasing EGCG concentration after freezing and thawing as well as after freeze drying and re-hydration (with the exception of the use of 0.945 mg/ml EGCG after freeze-drying). The percentage of cells that presented an intact membrane after freeze drying with 1.89 mg/l EGCG was about 90% in this experiment. This survival rate is comparable to the rate obtained after freeze thawing. All lyophilized samples that contained EGCG had more than 70% membrane integrity.

Experiment B2:

Samples of UCB (2.5 ml), prepared as described above, were suspended with a freezing solution composed of 0.1M trehalose and 0.945 mg/ml EGCG (Zhejiang Yixin Pharmaceutical Co., Ltd., China) in PBS ($Ca^{++}$ and $Mg^{++}$ free) or composed of 0.1M trehalose and 1.89 mg/ml EGCG (Zhejiang Yixin Pharmaceutical Co., Ltd, China) in PBS ($Ca^{++}$ and $Mg^{++}$ free). The samples were frozen using the MTG-516 device at a cooling rate of 5.1° C./min. After freezing, samples were stored briefly in LN until put in the commercial lyophilizer (Labconco, USA) for 3 days. After which, samples were rehydrated by adding 2.4 ml of double distilled water at 37° C. The samples were counted for viability using SYBR14/PI (Molecular Probes, USA) fluorescent dyes.

Figure 2B:
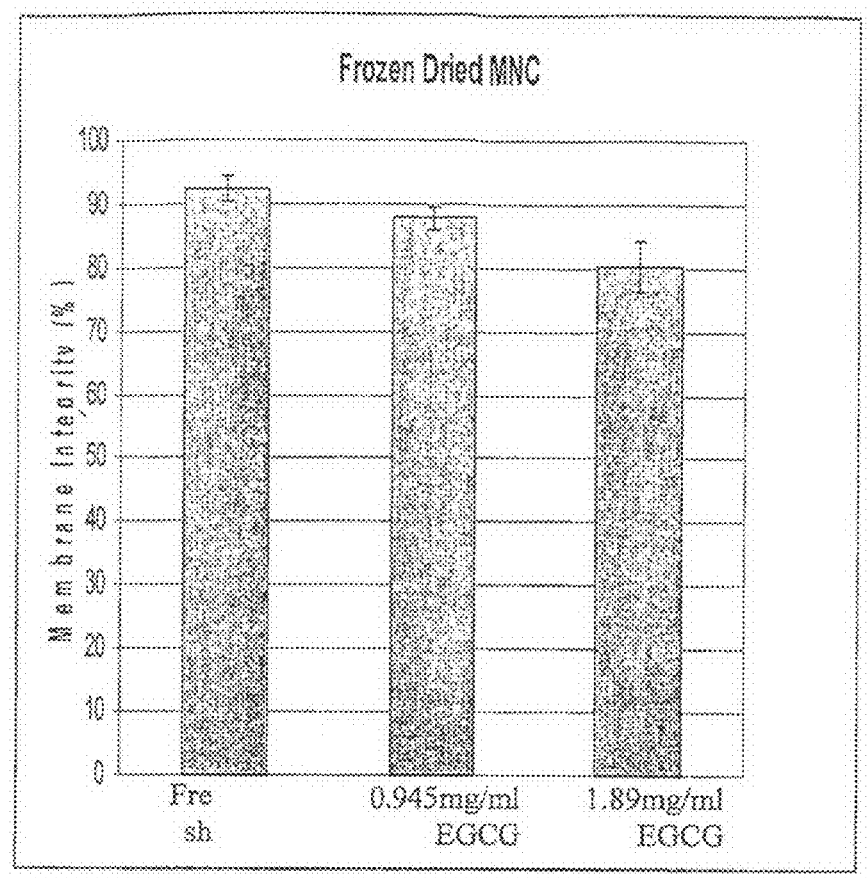

Results are presented in FIG. 2B as the mean and standard deviation. Each rehydrated column represents a sample (one freeze dried test tube). For each samples at least 300 cells were counted in different fields.

Experiment Conditions

| | |
|---|---|
| Freezing Device: | MTG-516 |
| Freezing Velocity: | 0.2 mm/sec |
| Temperature gradient (° C.) | T = 4°→ −10° → −40° → −70° C. |
| Sample volume: | 2.5 ml |
| Storage Temperature: | LN Tank |
| Lyophilization time: | 3 days |
| Rehydration method: | Addition of 2.4 ml DDW (37° C.) |
| Survival assay: | SYBR14/PI (Molecular Probes, USA) |

As seen in FIG. 2B, membrane integrity was very high in both EGCG concentrations, although the viability was a bit lower in the higher concentration. In light of the above, the 0.945 mg/ml EGCG solution was chosen for additional experiments.

Experiment C:

In this assay a freezing solution composed of 0.1M trehalose and either 0.47 mg/ml EGCG (×2.5) or 1.89 mg/ml EGCG (×10) in PBS were used. Sample's volume was 2.5 ml and samples were frozen and then lyophilized as described above. After being in the lyophilizer for 72 h, the samples were taken out and re-hydrated with 2.4 ml of DDW at 37° C. After re-hydration samples were assayed for CD3 using FACS (fluorescent-activated cell sorter) in accordance with the method described in Hulling et al. The Journal of Immunology 2003, 171: 4824-4829.

CD3 is a known cellular marker that is present in mature lymphocytes but not in other mononuclear cells, thus its presence indicates that mature lymphocytes are present in the sample.

Membrane integrity of the samples was evaluated before and after re-hydration using SYBR 14 and PI (Molecular Probes, USA). The membrane integrity and CD3 expression results are summarized in Table 1:

TABLE 1

Membrane Integrity and CD3 expression of UCB derived MNC

| Solution | Sample No. | Membrane integrity (%)* | CD3 (%) |
|---|---|---|---|
| Fresh with 0.47 mg/ml EGCG | 1 | 97.36 ± 2.2 | — |
| Lyophilized with 0.47 mg/ml EGCG | 1 | 55.1 ± 8.5 | 80 |
| | 2 | 59.8 ± 1.4 | 80 |
| Fresh with 1.89 mg/ml EGCG | 1 | 90.01 ± 4.3 | — |
| Lyophilized with 1.89 mg/ml EGCG | 1 | 79.31 ± 8.8 | 81 |
| | 2 | 83.62 ± 5.7 | 83 |
| | 3 | 88.4 ± 3.2 | 82 |
| | 4 | 88.03 ± 5.6 | 78 |

It is worth noting that membrane integrity results in each row represent results from at least 300 cells in 3 different places in the slide. The step of separation using the ficoll-paque is meant to separate the lymphocytes from most other cell types. The CD3 results indicate that mature lymphocytes were separated, and that they also survived the freeze drying (i.e. that the survival was not limited to other cell types). The mean of the 4 samples frozen with the higher EGCG concentration (1.89 mg/ml) indicates that about 84% of the cells show intact membranes after freeze drying and re-hydration as compared to about 90% of the cells with intact membranes to begin with (i.e. fresh, after separation but un-frozen cells). The measure of lymphocytes and their integrity after freezing is indicative of the condition of other cell types in the sample (e.g. stem cells).

Figure 3:
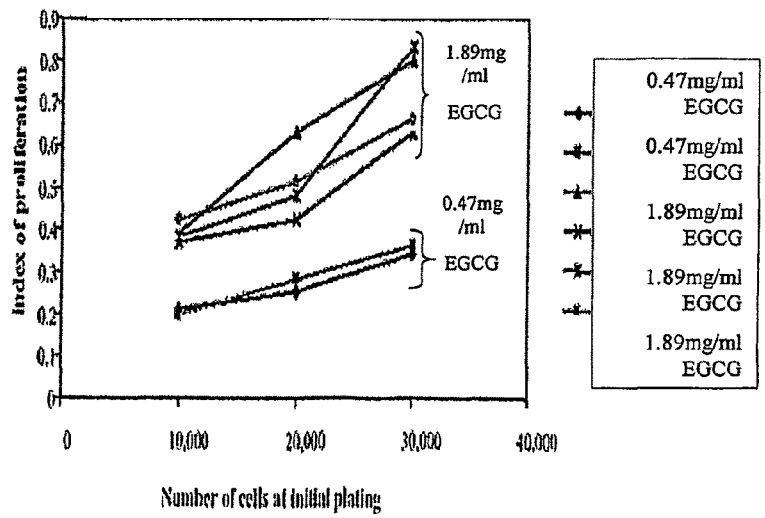
FIG. 3 is a graph showing the proliferation of mononuclear cells (MNC) after freezing and thawing and after lyophilization and re-hydration, according to some embodiments of the invention. (×2.5 EGCG=1.03 mM; ×10 EGCG=4.12 mM)

In addition, a cell proliferation assay was performed. In brief, the hydrated cells were incubated for 48 hour after which a proliferation assay based on thymidine incorporation was carried out (Promega, USA). The results of the proliferation assay are depicted in FIG. 3, wherein the proliferation index of the cells is depicted as a function of their number at initial plating. As can be seen, all cells lyophilized at a concentration of ×10 EGCG depicted a higher proliferation index than those lyophilized in ×2.5 EGCG.

In addition, as the cells' initial plating number increased so did the proliferation index. The almost linear proportion shown for one of the ×10 EGCG samples is similar to that observed with fresh cells (fresh cells not shown) This indicates that most of the lymphocytes that survive freeze drying maintain their ability to proliferate and is thus is indicative to the condition of other somatic cells (such as stem cells) in the sample.

Evaluation of Different Cooling Rates

The following experiments were done with mononuclear cells (MNC) from umbilical cord blood (UCB). The freezing solution that was used was composed of 12.5% (w/v) human serum albumin (HSA) (Kamada, Israel) and 0.1M Trehalose in PBS.

The freezing temperatures of the MTG-516 (IMT, Israel) were set to the same temperatures as described above. The different cooling rates were achieved by varying the velocities at which the samples were pushed along the predetermined temperatures. The velocities were: 0.02, 0.2 and 2 mm/sec, resulting in a cooling rate of 0.51, 5.1 and 51° C./min, respectively. All other procedures of this experiment were performed as described above. The MNC separation and freezing was done as described above.

Figure 4A:
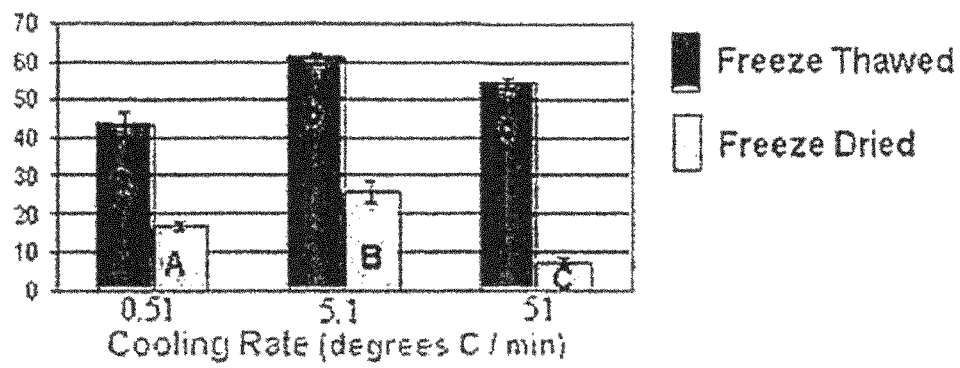
FIGS. 4A-4B are graphs showing membrane integrity (FIG. 4A) and percentage of cells that are metabolizing (FIG. 4B) after freezing at different cooling rates prior to thawing or drying (results are shown as the percentages of treated samples compared to the fresh samples).

Of all the cooling rates examined the best results were obtained at a cooling rate of 5.1° C./min for freeze thawing and freeze drying. At this cooling rate about 60% of the cells presented an intact membrane after freeze thawing and about 25% of the cells presented an intact membrane after freeze drying as seen in FIG. 4A.

Figure 4B:
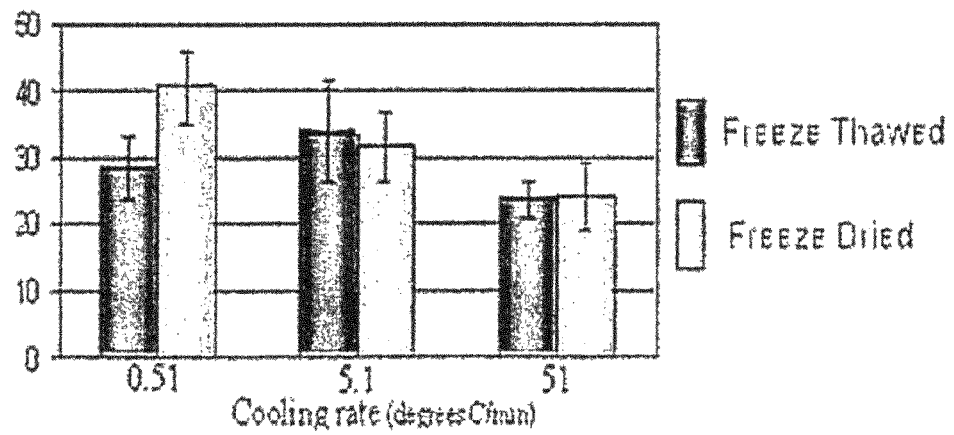

FIG. 4B shows a comparison of cell metabolism rate. At all cooling rates the percentage of cells that are metabolizing after freeze thawing is close to the percentage of cells that are metabolizing after freeze drying. This indicates that about the same percentage of cells maintain their capability to metabolize.

Colony Forming Units (CFU) Assay of Frozen Dried MNC Derived from UCB

This experiment was designed to evaluate the functionality of the surviving hematopoietic stem cells to differentiate into different white blood cells. This was done by evaluating the ability of the stem cells to form colonies, thus the name of the assay is colony forming unit (CFU) assay. In this specific assay the cells were evaluated for their ability to differentiate into granulocytes—macrophage colonies, (referred to as CFU-GM assay). This assay was performed at "Sheba" Medical Center. The assay involves 2 weeks of incubation of the cells, after which the colonies that were formed were counted using a light microscope.

Fresh UCB, from one donor, was separated as described above in order to receive the MNC layer. The cell pellet was suspended with a freezing solution composed of 0.1M Trehalose and 0.945 mg/ml EGCG (Zhejiang Yixin Pharmaceutical, China) both were dissolved in PBS. A total of 8 test tubes containing 2.5 ml of cell suspension were frozen and dried.

All experimental steps were performed as described above. Table 2 provides data relating to the integrity of the cells in the different samples (total of 8 tubes) after lyophilization, while Table 4 provides the number of CFU-GM colonies at the end of the assay (CFU-GM=Growth of granulocytes and macrophage colonies). It is noted that in the results in Table 3 the fresh cells were whole (un-separated) UCB. The results are shown as the mean of live cells out of the total cells counted. At least 300 cells were counted in 3 different fields to calculate the mean and standard deviation.

TABLE 2

Membrane integrity rates of fresh and lyophilized samples

| Treated sample | Membrane integrity (%) |
| --- | --- |
| Fresh | 94.28 ± 2.53 |
| Lyo # 1 | 90.06 |
| Lyo # 2 | 89.63 |
| Lyo # 3 | 87.14 |
| Lyo # 4 | 91.08 |
| Lyo # 5 | 89.43 |
| Lyo # 6 | 89.91 |
| Lyo # 7 | 90.11 |
| Lyo # 8 | 89.91 |
| Lyo Samples mean | 89.65 ± 1.13 |

TABLE 3

Number of CFU-GM colonies

| Sample | Total colonies | Type |
| --- | --- | --- |
| Fresh MNC | 20 | CFU-GM |
| Lyophilized MNC | 7 | CFU-GM |

Figure 5:
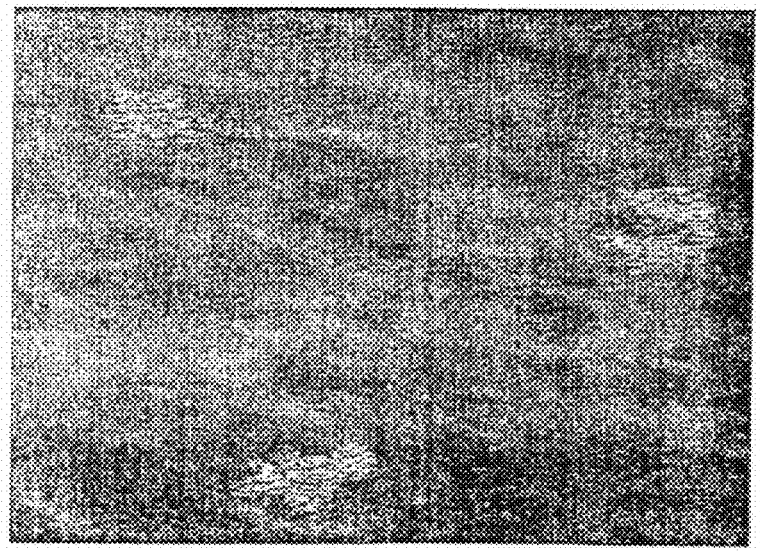
FIG. 5 is a photograph of CFU-GM colonies grown from previously lyophilized MNC as viewed by a light microscope.

Further results are demonstrated in FIG. 5, specifically showing that freeze-dried MNC, re-hydrated with double distilled water were able to develop into colonies. Thus, indicating that the HSC survive lyophilization and were able to proliferate.

Lyophilization of Mice Bone Marrow

The following experiment was designed to evaluate the survival of MNC derived from bone marrow after freeze drying. Fresh mouse bone marrow cell suspension (7.5 ml diluted with PBS) contained approximately $50 \times 10^6$ cells. This cell suspension (5 ml) was centrifuged (200 g, 10 min) and pellet was suspended with 6 ml freezing solution composed of 0.1M trehalose and 0.945 mg/ml EGCG in PBS. Two samples were then freeze-dried. All other experimental procedures were done as described above.

Table 4 provides data concerning membrane integrity of cells after the indicated treatments.

TABLE 4

Membrane integrity of fresh and lyophilized mice bone marrow stem cells

| Treatment | % Membrane integrity |
| --- | --- |
| Fresh cells with freezing solution | 86.27 ± 6.74 |
| Frozen dried Sample A | 77.38 ± 7.51 |
| Frozen dried Sample B | 79.64 ± 2.76 |

Membrane integrity rates were quite high; about 78% of the cells maintained an intact membrane. Bone marrow is a rich source of HSC. Therefore, it is reasonable to expect that many of the surviving cells are HSC. It is noted that in vivo experiments (see below) also support this assumption. In addition, it is observed that the same method of lyophilization produces good viability rates both for human cells and for mice cells.

Freeze Thawing and Freeze Drying of Macrophage Units

Macrophages

Macrophage units were supplied by Professor Danon, Israel blood services, Tel-Hashomer, Israel. In the following experiments all buffy coats and/or macrophage units referred to were manipulated using the method and system for cultivating macrophages described in U.S. Pat. No. 6,146,890 which is incorporated herein by reference in its entirety, whereby hypo-osmotic shock is used to enhance the cells' differentiation into macrophages. Such manipulated cells were reported not to maintain viability after a conventional freezing process therefore their shelf life is very short, limiting their applications.

Blood Separation

A part of the buffy coat was separated in order to produce mononuclear cells which include the monocyte/macrophage layer. The blood was separated on a Ficoll-Paque gradient for 30 minutes at 1000 g, afterwards the mononuclear layer was drawn out and washed twice in Phosphate Buffered Saline (PBS) (Calcium and Magnesium free, Bet Haemek, Israel) for 10 minutes at 200 g. The pellet was then resuspended with 3 ml of culture medium (RPMI 1640 with glutamine, 10% fetal calf serum and 1% antibiotic, all supplied by Bet Haemek, Israel). The rest of the buffy coat was left untouched.

Incubation

Whole buffy coat or mononuclear cells in culture medium were incubated for one hour with different concentrations of Trehalose (0.1, 0.3, 0.5 and 1M). Incubation was done at 37° C., 5% $CO_2$ humidified incubator.

Freeze Thawing and Freeze-Drying

Buffy coat samples and MNC samples were frozen by using the MTG-516 freezing apparatus (IMT, Israel) at a cooling rate of 5.1° C./min. Samples were rotated during freezing at 56 rounds per minute. After freezing, all samples were plunged into liquid nitrogen. Thawing was done at 37° C. in a water bath. Lyophilization was done by putting the frozen samples in a commercial lyophilizer (Labconco, USA) with a condenser temperature of −80° C. After drying, the cells were rehydrated with ultra pure water at 37° C. in order to regain their original volume (2.5 ml).

Viability Assessments

Viability assessments were done by evaluating the membrane integrity of the cells using SYBR14/Propidium Iodide (PI) (Molecular Probes, USA) live/dead fluorescent staining. These stains are nucleic acid stains, SYBR14 is a membrane permeable molecule and PI can enter the cell only if the membrane is damaged.

Figure 6A:
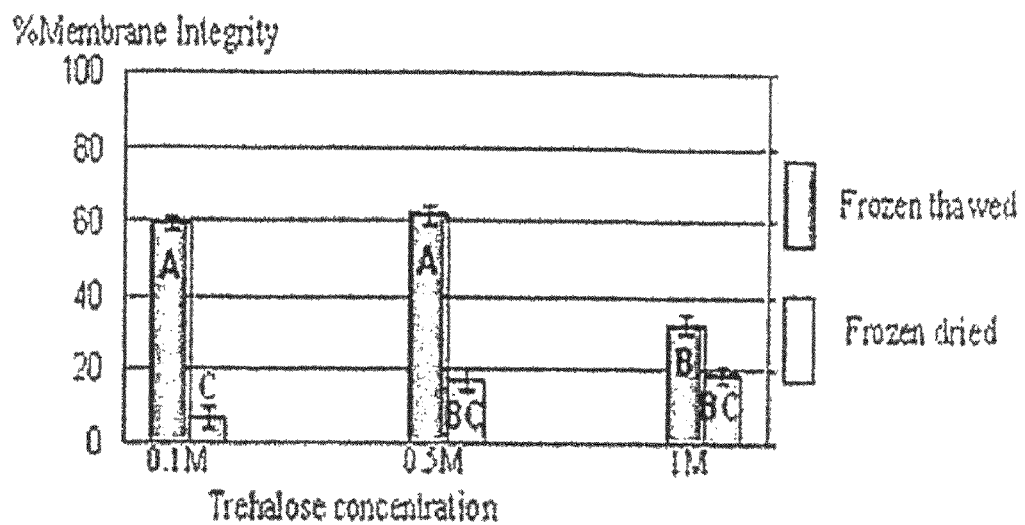
FIGS. 6A-6C are bar graphs showing the percentage of membrane integrity in macrophages that were frozen and thawed and macrophages that were freeze dried with different trehalose concentrations where macrophages were separated on Ficoll-Paque gradient prior to freezing (FIG. 6A) or without prior separation on Ficoll-Paque gradient (FIG. 6B); or tells were frozen as whole macrophage units (FIG. 6C).
Figure 6B:
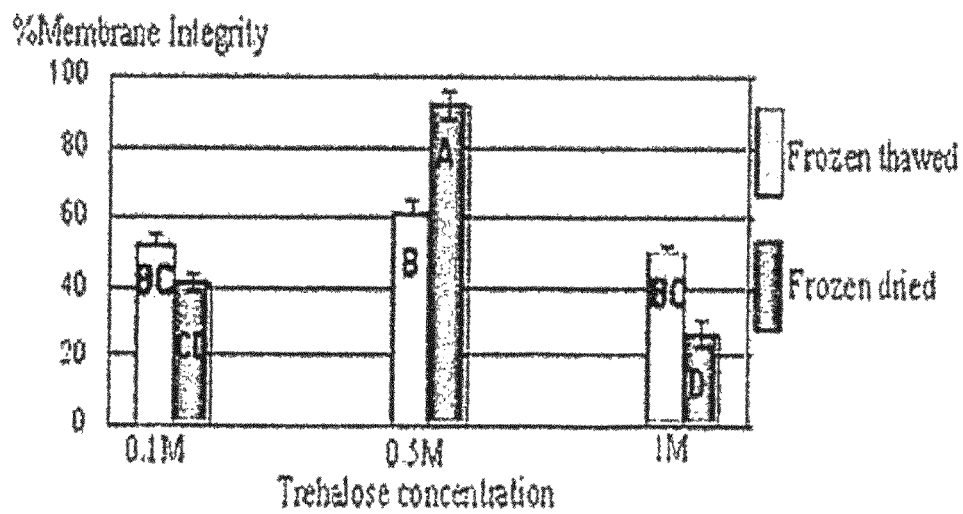
Figure 6C:
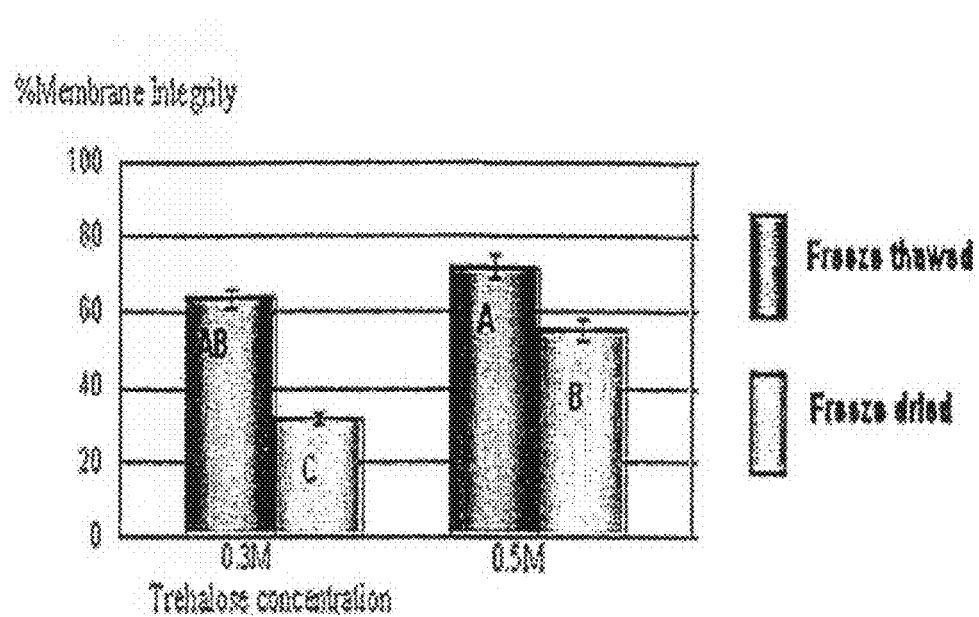

Cell survival after freeze-thawing of macrophages was at an average of 60% in our experiments, whether separated on Ficoll-Paque gradient prior to freezing (FIG. 6A) or not (FIGS. 6B and 6C). With best result of 72.03±2.8% membrane integrity achieved with samples frozen-thawed with 0.5M trehalose (FIG. 6C).

Cell survival after freeze-drying was higher in cells that were frozen without Ficoll-Paque treatment (FIGS. 6B and 6C in comparison to FIG. 6A). It appears that the best survival rates are achieved with a concentration of 0.5M Trehalose (FIGS. 6B and 6C). In the second experiment, cell survival at that concentration was lower than that of the first one (55.35±2.9% (FIG. 6C) in contrast to 91.86±4.2% (FIG. 6B. Yet, these survival rates indicate that lyophilization of these cells is possible.

CD34+ Detection of Frozen and Frozen Dried MNC Derived from UCB

The purpose of this experiment was to evaluate the percentage of the CD34+ cells that survive lyophilization. CD45+\CD34+ cells are representative of the HSC within the MNC.

Fresh UCB (received from "Sheba" Medical Center) was separated using Histopaque 1077 solution. MNC layer was collected and washed with PBS (Calcium and Magnesium free). Cell pellet was suspended with our freezing solution (0.1M Trehalose+0.945 mg/ml EGCG (Zhejiang Yixin Pharmaceutical, China), both were dissolved in PBS). Samples were frozen in the MTG device (IMT, Israel) with the following parameters: velocity=0.22 mm/sec, Temperatures=4°→−10°→−40°→−70° C., Rotation=60 rpm, resulting at a cooling rate of 5.1° C./min. Samples were stored in LN prior to lyophilization. Cells will be lyophilized for 3 days in a commercial lyophilizer (Labconco, USA). Rehydration was done by addition of 2.4 ml sterile DDW.

Cell survival was assayed by membrane integrity stains using SYBR 14/PI (Live/Dead) stain (Molecular Probes, USA). In addition, the ratio of CD34+ cells (stem cells marker) was evaluated by FACS. Table 5 shows membrane integrity of the different MNC after the indicated treatments. Table 6 shows CD34+/CD45+ cell number within the NMC population.

TABLE 5

Membrane integrity of fresh and lyophilized NMC

| Treated sample | Membrane integrity (%) |
|---|---|
| Fresh MNC | 95.03 |
| Lyophilized MNC #1 | 84.98 |
| Lyophilized MNC #2 | 85.01 |

TABLE 6

Determination of CD34+/CD45+ cell number within the NMC population

| Sample | Total MNC ($10^6$/ml) | % CD34 | CD34 Total (cell number/ml) |
|---|---|---|---|
| Fresh UCB | 5.8 | 0.21 | 12400 |
| Fresh MNC (Ficol) | 2.3 | 0.68 | 15600 |
| Lyophilization #1 | 2.5 | 0.69 | 17300 |
| Lyophilization #2 | 2.5 | 0.70 | 17600 |

As can be seen in Tables 5 and 6 a high amount of the cells (85%) have maintained their membrane integrity (table 5) after lyophilization. In addition, there was no reduction in the amount of HCS, as indicated by CD34+ cells, after lyophilization as compared to the fresh MNC sample.

Testing the In Vivo Survival and Functioning of the Frozen Dried HSC

In order to demonstrate the application of cell therapy using the successfully freeze-dried MNC the following experiment is performed. In this model reconstituted human MNC derived from UCB is injected into immuno-suppressed mice.

Human UCB units are separated on ficoll-paque gradient to receive the MNC layer and treated as follows:

The MNC are divided into 2 groups (one group is freeze-dried and the other kept fresh).

The first group of cells are frozen using the MTG-516 (IMT, Israel) and lyophilized using a commercial lyophilizer (Labconco, USA), all as detailed in any one of the above experiments. Re-hydration is done by adding double distilled water at 37° C. to essentially the same volume as before freeze-drying (i.e. 2.5 ml).

The second group is maintained as liquid fresh cells (in buffer or medium, such as RPMI medium that may be supplemented with fetal calf serum and antibiotics) at 4° C. to room temperature, to be used as the control.

From each group $0.5$-$40 \times 10^6$ (e.g. $20 \times 10^6$) cells are injected (using intravenous, intramuscular, transdermal, subcutaneous, or intraperitoneal injection) either by one or more injections (e.g. bolus) or in form of an infusion (continuously) into immune compromised mice (e.g. Non-obese diabetes (NOD)-SCID mice that receive a sub-lethal dose of radiation (375 cGy)

4-8 weeks after injection mice are sacrificed and one or more organs or tissues (e.g. bone marrow or spleen) are analyzed using FACS or any other assay known in the art for human CD19 and CD45 cell markers (using mice anti human antibodies for these markers). CD 19 is a marker for pre-mature B cell and CD45 is a marker that is expressed on all lymphocytes. The presence of cells having either marker indicates that the human cells have migrated into the mouse bone marrow and differentiated. The results of the freeze-dried group are compared to the results of the fresh group thus showing the fraction of stem cells that maintained viability, showing that freeze dried cells survive and differentiate in the mouse, enabling cell therapy.

Optionally a third group of mice may be used as a control, and not injected with MNC (or injected with saline or a buffer or medium as that in which the fresh cells are held).

The detailed protocols that are used in this experiment for FACS, mice (breeding, handling and treatments) and for human cell engraftment evaluations are found in the article by Avigdor at al., (2004).

Lyophilization of Mice Bone Marrow

Survival of reconstituted mononuclear cells derived from mice bone marrow was evaluated in vitro and in vivo. To this end, leg bones from 5 male NOD-SCID mice (Balb$_c$x57B1) were used for the extraction of bone marrow. The culture medium for the bone marrow contained RPMI-1640 medium with L-glutamine, supplemented with 1% commercial antibiotics mix (Penicillin, Streptomycin, Nystatin) and 20% fetal calf serum.

About 5 ml culture medium was injected to the center of each bone in order to collect the bone marrow cells (BM). The collected BM was centrifuged at room temperature for 10 minutes at 1000 g. The supernatant was removed and the cell pellet was suspended with 2 ml of the above supplemented medium. Cell counting was done by trypan blue according to the manufacturer's protocol. 20 µl from the resuspended cells were added to 380 µl solution of 4% trypan blue and the cells were counted using a hemocytometer in a light microscope.

After another centrifugation (1000 g, 10 min), each cell pellet was suspended with 10 ml of freezing solution composed of: 0.1M Trehalose and 0.945 mg/ml EGCG (Zhejiang Yixin Pharmaceutical, China), in PBS (calcium and magnesium free). The collected bone marrow was combined in a single sample, and the final cell count was approximately $3.04 \times 10^6$/ml. Three samples of 2.5 ml each were put is a 16 mm glass test tube (Manara, Israel) and were frozen using the MTG-516 freezing device. Samples were stored for 30 min in LN prior insertion into a commercial lyophilizer (Labconco, USA) for 4 days. Samples were sent maintained dry at room temperature under vacuum and in the dark for about 2 hours and were then re-hydrated by addition of 2.4 ml sterile warm DDW (35% survival) to each sample. Cell survival was assayed by SYTO/PI and by trypan blue. The functionality of the surviving cells was tested by injecting reconstituted cells (including the freezing solution) into irradiated NOD-SCID female mice (Balbcx57B1). The recipient mice were irradiated one day prior injection of the cells with 900cGy to the entire body and divided into 2 groups each composed of 5 mice. The first group was left un-touched, and the second group was injected with 0.5 ml of the reconstituted cells. The mice were then observed to see their survival. Cell viability was also determined (Table 7).

Experimental Conditions

| Freezing Device | MTG-516 |
| --- | --- |
| Freezing Velocity | 0.2 mm/sec, Rotation = 60 rpm |
| Freezing parameters | 4° C.→ −10° C.→ −40° C. → −70° C. |
| Sample volume | 2.5 ml |
| Storage Temperature | LN |
| Lyophilization | Commercial device (Labconco) |
| Cell count | ABX-Pentra 60 |
| Cell staining | Trypan blue |

TABLE 7

Viability as indicated by membrane integrity of lyophilized mice bone marrow cells

| Before Freezing | After lyophilization |
| --- | --- |
| 90.01 ± 4.4 | 43 ± 10.4 |

Figure 7:
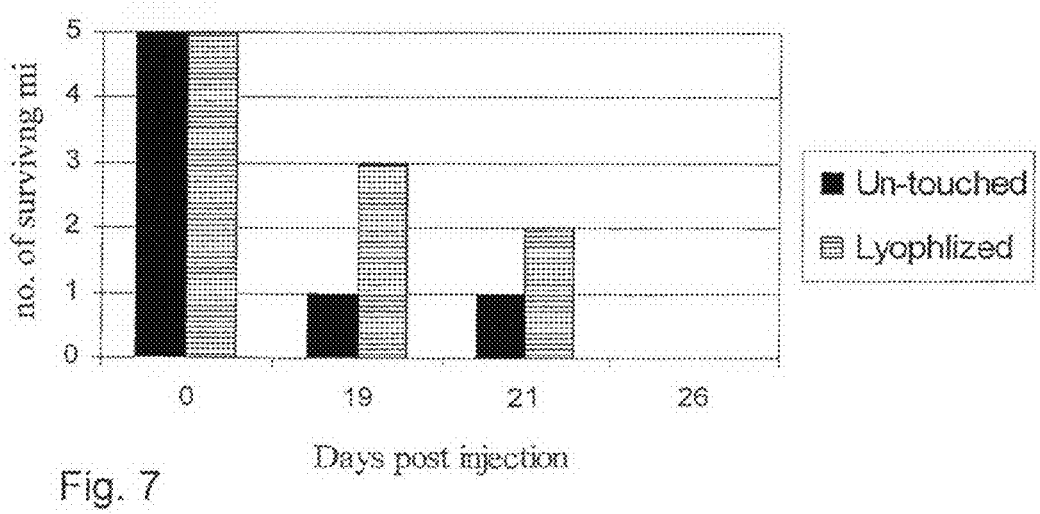
FIG. 7 is a bar graph demonstrating the survival patterns of mice injected with bone marrow derived MNC compared with mice that were not administered with NMC.

There was a decrease in cells viability after lyophilization (from 90% in fresh cells to 43% after lyophilization and reconstitution). As demonstrated in FIG. 7 mice that were injected with MNC had a longer life expectancy then the mice that were not injected at all, and at 19 days (above 2 weeks) from irradiation, 3 times more mice were alive from the test group. The survival pattern indicates that administration of reconstituted lyophilized MNC improves the function of the immune system at least in the short term as opposed to un-treated mice.

Freeze Thawing of Mice Bone Marrow

Bone marrow derived from male NOD-SCID mice (Balbcx57B1) was collected as detailed above. The supernatant was removed and the cell pellet was suspended with 2 ml of the above supplemented medium. After centrifugation, every cell pellet was suspended with 5 ml of freezing solution composed of: 0.1M Trehalose and 0.945 mg/ml EGCG (Zhejiang Yixin Pharmaceutical, China), in PBS (calcium and magnesium free), such that the final cell concentration was approximately $2.09 \cdot 10^6$/ml. 2 samples each containing a volume of 2 ml cells suspension were frozen in the MTG-516 device. The samples were stored in LN for 4 days, thawed in a 37° C. water bath, and combined. Cell survival was assayed by Trypan Blue staining. The functionality of the thawed cells was assayed by injecting thawed cells into female irradiated NOD-SCID mice (Balb$_c$x57B1) irradiated as detailed above one day before injection. The irradiated mice were divided into 2 groups, each composed of 5 mice. The first group was left un-touched and the second group 0.5 ml of the thawed cells was injected. The mice were then observed to see their survival. With the exception of a single mouse from the control group, all mice survived for at least 3.5 weeks after irradiation.

At 3.5 weeks after injection of the thawed cells blood samples were taken from the mice for PCR analysis for indication of Y chromosome, being present only in the injected male blood cells. As positive controls for blood from a male mouse genetically identical to the BM donor mice and pure DNA with Y chromosome were used. As a negative control blood was taken from two un-injected female mice.

Experimental Conditions

| Freezing Device | MTG-516 |
| --- | --- |
| Freezing Velocity | 0.2 mm/sec |
| Temperature | 4° C.→ −10° C.→ −40° C. → −70° C. |
| Rotation | 60 rpm |
| Sample volume | 2 ml |
| Storage Temperature | LN |
| Thawing | Water bath (37°) |
| Cell count | ABX-Pentra 60 |
| Cell staining | Trypan Blue |

TABLE 8

Membrane integrity of fresh and lyophilized thawed mice BM cells
Mice BM in freezing solution

| Prior Freezing | | After Thawing | |
| --- | --- | --- | --- |
| cell concentration ($10^6$/ml) | Viability (%) | cell concentration ($10^6$/ml) | Viability (%) |
| 2.64 | 82.81 ± 8 | 2.75 | 53.5 |

As seen in Table 8, there was no significant change in the cells concentration before and after freezing, and after thawing 64.6% of the cells were viable as compared to the fresh cells.

In the PCR assay (results not shown) 2 of the injected female mice displayed presence of Y chromosome in their blood cells. The control female blood did not display this chromosome. This indicates successful engraftment of the thawed BM, in at least 2 out of 5 mice, because only stem cells that have successfully engrafted into the bone marrow could produce blood cells having Y chromosome at 3.5 week after transplantation.

Freeze Thawing of Mesenchymal Cells

Human Mesenchymal stem cells (MSC) were supplied by Pluristem Life Systems Inc. in a 600 ml flask with Filter cap for continuous venting (NUNC) were incubated (37° C., 5% $CO_2$) overnight. The medium was aspirated. The adherent cells were suspended using 6 ml of Trypsin-EDTA (Solution A, Biological Industries Ltd., Israel) for 5 min and then fresh RPMI medium (12 ml) was added to the flask in order to deactivate Trypsin. The suspended cells were divided to two 50 ml tubes, and centrifuged at 1200 rpm for 8 min. One of the pellets was suspended with 5 ml of sterile freezing solution, and a 2 ml aliquot was taken for freezing. The aliquot was frozen in the MTG-516 device and transferred to LN for 8 days. Thawing was in a water bath (37° C.). The viability of the fresh (before and after addition of the freezing solution) and thawed cells was assayed by SYTO/PI staining and the results are shown in Table 9.

Experimental Conditions

| Freezing Device: | MTG-516 |
| --- | --- |
| Freezing solution: | 0.945 mg/ml of EGCG + 0.1M of trehalose |

-continued

| | |
|---|---|
| Freezing conditions: | |
| Freezing Velocity: | 0.22 mm/sec |
| Rotation rate: | 60 rpm |
| Temperature gradient: | 4° → −10° → −40° → −70° C. |
| Sample volume: | 2 ml |
| Storage conditions: | LN |
| Thawing method: | Water bath |
| Thawing time: | 60 sec |
| Cell count and MCV values: | ABX-Pentra 60 device and manual count |
| Survival assay: | SYTO/PI staining |

TABLE 9 concentration and viability of mesenchymal cell

| | Fresh | | Thawed | |
|---|---|---|---|---|
| Sample | Cell concentration ($10^6$/ml) | % viability | Cell concentration ($10^6$/ml) | % viability |
| control | 0.2 | 69.85 | | |
| freezing solution | 0.5 | 82.2 | 0.6 | 41.5 |

In Situ Freeze Drying of MSC

MSC taken from incubation (as described above for the freeze thawing protocol, 37° C., 5% $CO_2$) are left on the plate. The medium is aspirated and the cells are then optionally washed at least once with 20 ml of PBS or freezing solution (0.1M trehalose and 0.945 mg/ml of EGCG). The washing solution is aspirated and fresh freezing solution (e.g. 2 or 2.5 ml to a 35 mm diameter Petri dish) is added. Alternatively, before freezing, even a higher freezing solution is added to the plate, but most of the freezing solution is aspirated before freezing, living only trace amounts of the solution in the plate. The dish is then placed in conventional mechanical freezer (−80° C.) until frozen. After complete freezing, the cells are lyophilized in a commercial lyophilizer (Labconco, USA, with condenser set to −80° C.) until dry (e.g. 3 days).

For rehydration, in the case of freezing with the freezing solution DDW is added in a volume similar to the freezing solution (e.g. 1.9 or 2.4 ml). Where the freezing solution is aspirated prior to freezing, any solution known not to damage the cells may be used (e.g. saline or medium).

Embryonic Development Nuclear Transfer Using Freeze Dried Granulosa Cells and Donor Cells Fresh sheep granulosa cells were freeze dried according to the above protocol for UCB, with a freezing solution composed of 0.1M Trehalose and 0.945 mg/ml EGCG (Zhejiang Yixin Pharmaceutical, China in PBS (calcium and magnesium free)). 2.5 ml of cells suspension were frozen in 16 mm diameter glass test tubes (Manara, Israel) using the MTG-516 apparatus. After freezing, the samples were stored in LN tanks and later lyophilized (Labconco, USA) for 3 days. In the lyophilizer the samples were placed next to the condenser. After lyophilization, the dry samples were stored under vacuum, at RT and in the dark for at least 12 to 18 months before being used as nucleus donors in nuclear transfer. Cells were hydrated with sterile DDW (Milli-Q grade), and immediately injected into enucleated oocytes [Loi, P., et al. Biology of Reproduction 58: 1177-1187 (1998); Ptak, G., et al. Biology of Reproduction 67: 1719-1725 (2002)]. As a control, the same protocol was carried out using as donors granulosa cells from a different donor.

Results

Enucleated oocytes reconstructed with freeze dried granulosa cells initiated cleavage at similar rates to control embryos generated using fresh granulosa cells. Development to the blastocyst stage was somewhat lower for freeze dried reconstructed embryos than for control embryos (16% and 21% respectively).

Freeze Thawing Large Volume (30 ml)

Fresh UCB (Sheba Medical Center) were separated on a Ficoll-Paque gradient using Histopaque-1077 solution. The MNC layer was collected and washed once with PBS (Calcium and Magnesium free), and suspended with a freezing solution (0.1M trehalose and 0.945 mg/ml EGCG (Zhejiang Yixin Pharmaceutical Co., Ltd, China) in PBS (calcium and magnesium free)).

The cells of were frozen in MTG device in a volume of 30 ml ($2.1 \cdot 10^6$ cells/ml) in a glass tube (Diameter=22 mm, length=148 mm), and stored over night in an LN tank. Thawing was performed by placing the tube 2.5 minutes at room temperature (in the air) and then slowly inserting the tube into a pre warmed water bath (41° C.) until complete thawing (ca. 300 seconds). The viability of the fresh and thawed cells was assayed by Trypan blue (TB) as described previously.

Experimental Conditions

| | |
|---|---|
| Freezing Device: | MTG |
| Freezing Velocity: | 0.2 mm/sec |
| Temperature gradient (° C.) | T = 4° → −10° → −40° → −70° C. |
| Sample volume: | 30 ml |
| Storage: | Over night (18 hours) in LN Tank |
| Thawing method: | Room temp and water bath (37° C.) |
| Thawing time: | 2.5 min in air and 300 sec in water bath |
| Cell counts: | Pentra 60 (ABX, France) & hemocytomer |
| Survival assay: | TB |

TABLE 10

MNC properties before and after freeze thawing

| Fresh MNC | | | Thawed MNC | | |
|---|---|---|---|---|---|
| Cell concentration ($10^6$/ml) | % MNC | % viability (TB) | Cell concentration ($10^6$/ml) | % MNC | % viability (TB) |
| 2.1 | 95.7 | 92.55 ± 2.1 | 2 | 98.3 | 83.4 ± 6.7 |

As seen in Table 10, freeze thawing of large volume of MNC derived from UCB has yielded high viability rates, and membrane integrity results were very high (90% compared to fresh cells).

The Effect of Cooling Rate on Freeze Thawing of MNC in Large Volume (50 ml) Samples A fresh UCB unit was received from Sheba Medical Center and separated on a Ficoll-Paque gradient using Histopaque-1077 solution. The MNC layer was collected and washed once with PBS (Calcium and Magnesium free), and the pellet was suspended with a freezing solution (0.1M trehalose and 0.945 mg/ml EGCG (Zhejiang Yixin Pharmaceutical Co., Ltd, China) in PBS (calcium and magnesium free)). Sample volume was 50 ml and cells suspension concentration was $1 \cdot 10^6$ cells/ml. The sample was placed in a cryopreservation bag and freezing was performed using a modified MTG apparatus (essentially as disclosed in WO2005/072790) and stored in −80° C. conventional mechanical freezer overnight. The bag was thawed the following day by immersion in a water bath with forced water flow which was pre warmed to 37° C. for 90 sec. Viability was assayed by Trypan blue and SYTO/PI staining.

Experimental Conditions

| | |
|---|---|
| Freezing Device: | as described in WO2005/072790 |
| Freezing Velocity: | 0.2 mm/sec |
| Temperature gradient (° C.) | T = −6° C.→ −35° C. → −70° C. |
| Sample volume: | 50 ml |
| Storage Temperature: | −80° C. Freezer |
| Thawing method: | Bath (37° C.) |
| Thawing time: | 90 sec |
| Cell count and MCV values: | Pentra 60 (ABX, France) & hemocytomer |
| Survival assay: | TB, SYTO/PI staining (Molecular Probes, USA) |

TABLE 11 viability of MNC

| | Cell concentration | | viability | |
|---|---|---|---|---|
| Sample (50 ml) | (×10$^6$/ml) | % MNC | SYTO/PI | TB |
| Fresh MNC | 0.9 | 89.9 | 89.4 ± 10.4 | 92.02 ± 8.6 |
| Thawed MNC | 1 | 88.6 | 71.63 ± 13.6 | 83.01 ± 10.5 |

As seen in Table 11 survival rates were very high after freeze thawing in both methods of staining (the results of the thawed MNC were 80% of those of the fresh cells when using SYTO/PI and 90% when using TB). Thus, when the proper freezing parameters are maintained (i.e. temperature gradient and ice interface velocity) survival rates of MNC may be high even at volumes of 50 ml and higher. In addition over night storage of the frozen cells (50 ml)-80° C. did not cause a significant decline in survival comparing to previous data obtained in smaller volumes.

The invention claimed is:

1. A preserved cell preparation, comprising:
   lyophilized cells; and
   at least one polyphenol selected from the group consisting of epigallocatechin gallate (EGCG), epicatechin gallate (ECG), epigallocatechin (EGC), epicatechin (EC), DL-Catechin (DL-C) and gallocatechin gallate (GCG), or mixtures thereof, the polyphenol being present in a concentration of from about 50 μM to about 4 mM,
   the preserved cell preparation being essentially free of one or more cryoprotecting agents selected from the group consisting of polyalcohols, DMSO and cryoprotecting proteins, and
   upon reconstitution of the preserved cell preparation, at least 60% of the lyophilized cells in the preserved cell preparation are viable and sufficient for use in cell therapy.

2. The preserved cell preparation of claim 1, wherein the polyphenol is EGCG.

3. The preserved cell preparation of claim 2, further comprising trehalose.

4. The preserved cell preparation of claim 1, wherein the lyophilized cells are obtained by cooling cells at a cooling rate of 5.1° C./min.

5. The preserved cell preparation of claim 3, obtainable by freezing cells to obtain frozen cells and then freeze drying the frozen cells to obtain the preserved cell preparation.

6. The preserved cell preparation of claim 1, wherein the lyophilized cells comprise stem cells selected from the group consisting of hematopoietic stem cells, embryonic stem cells, embryonic germ cells and mesenchymal stem cells.

7. The preserved cell preparation of claim 1, wherein the lyophilized cells comprise human stem cells.

* * * * *